United States Patent
Dong et al.

(10) Patent No.: US 9,416,405 B2
(45) Date of Patent: Aug. 16, 2016

(54) COMPOSITIONS, METHODS AND KITS FOR ENHANCING PCR SPECIFICITY

(71) Applicant: LIFE TECHNOLOGIES CORPORATION, Carlsbad, CA (US)

(72) Inventors: Shoulian Dong, Mountain View, CA (US); Chunmei Liu, Palo Alto, CA (US)

(73) Assignee: Life Technologies Corporation, Carlsbad, CA (US)

( * ) Notice: Subject to any disclaimer, the term of this patent is extended or adjusted under 35 U.S.C. 154(b) by 132 days.

(21) Appl. No.: 14/071,444

(22) Filed: Nov. 4, 2013

(65) Prior Publication Data

US 2014/0134614 A1 May 15, 2014

Related U.S. Application Data

(60) Provisional application No. 61/740,242, filed on Dec. 20, 2012, provisional application No. 61/721,968, filed on Nov. 2, 2012.

(51) Int. Cl.
*C12P 19/34* (2006.01)
*C12Q 1/68* (2006.01)

(52) U.S. Cl.
CPC ............... *C12Q 1/6855* (2013.01); *C12P 19/34* (2013.01); *C12Q 1/686* (2013.01); *C12Q 1/6851* (2013.01); *C12Q 1/6858* (2013.01); *C12Q 1/6832* (2013.01); *C12Q 1/6848* (2013.01)

(58) Field of Classification Search
CPC .................. C12Q 2525/301; C12Q 2525/191; C12Q 1/6851; C12Q 1/6855; C12Q 1/6858; C12Q 1/6832; C12Q 1/6848; C12Q 1/686; C12P 19/34
USPC .................................................. 435/91.2, 6.1
See application file for complete search history.

(56) References Cited

U.S. PATENT DOCUMENTS

| | | |
|---|---|---|
| 2005/0272075 A1 | 12/2005 | Jacobsen et al. |
| 2007/0031857 A1 | 2/2007 | Makarov et al. |
| 2007/0059752 A1 | 3/2007 | Cook |
| 2007/0117112 A1 | 5/2007 | Diener et al. |
| 2008/0160529 A1* | 7/2008 | Brow .................. C12Q 1/6818 435/6.12 |
| 2008/0248469 A1 | 10/2008 | Spier |
| 2010/0279305 A1 | 11/2010 | Kuersten |
| 2013/0045885 A1 | 2/2013 | Mohapatra et al. |
| 2014/0134614 A1 | 5/2014 | Dong et al. |

FOREIGN PATENT DOCUMENTS

| | | |
|---|---|---|
| CN | 100580089 | 1/2010 |
| WO | WO-2004/013354 | 2/2004 |
| WO | WO-2007/127999 | 11/2007 |
| WO | WO-2008/045251 | 4/2008 |
| WO | WO-2008/097957 | 8/2008 |
| WO | WO-2011/100057 | 8/2011 |
| WO | WO-2014/071322 | 5/2014 |

OTHER PUBLICATIONS

Blewett, N. et al., "A quantitative assay for measuring mRNA decapping by splinted ligation reverse transcription polymerase chain reaction: qSL-RT-PCR", *RNA Journal*, vol. 17, No. 3, Cold Spring Harbor Laboratory Press, Mar. 2011, 535-543.

Huang, Y. et al., "The discovery approaches and detection methods of microRNAs", *Molecular Biology Reports*, vol. 38, No. 6, Nov. 25, 2010, 4125-4135.

Maroney, et al., "Direct detection of small RNAs using splinted ligation", *Nature Protocols*, vol. 3, No. 2, 2008, 279-287.

PCT/US2013/068350, "International Search Report mailed", Feb. 24, 2014, 6 pages.

PCT/US2013/068335, "International Search Report and Written Opinion mailed Jan. 23, 2014", 14 pages.

Li, D et al., "Study on High Resolution Melting and Applications of the Same", *Biotechnology Bulletin*, No. 7, Jan. 4, 2009, 8 pages.

* cited by examiner

*Primary Examiner* — Cynthia B Wilder

(57) ABSTRACT

The present disclosure provides novel primers and method for the detection of specific nucleic acid sequences. The primers and methods provided herein are useful in a wide variety of molecular biology applications and are particularly useful in allele-specific PCR.

15 Claims, 10 Drawing Sheets

COMPOSITIONS, METHODS AND KITS FOR ENHANCING PCR SPECIFICITY

RELATED APPLICATIONS

This application claims the benefit under 35 U.S.C. 119(e) of U.S. Provisional Patent Application No. 61/740,242, filed Dec. 20, 2012, and the benefit under 35 U.S.C. 119(e) of U.S. Provisional Patent Application No. 61/721,968, filed Nov. 2, 2012, each of which is hereby incorporated by reference in its entirety.

FIELD

This disclosure generally relates to the field of molecular biology. In particular, this disclosure relates to novel primers for use in the detection and discrimination of nucleic acids.

BACKGROUND

Assays capable of detecting and quantifying the presence of a particular nucleic acid molecule in a sample are of substantial importance in forensics, medicine, epidemiology and public health. Such assays can be used, for example, to identify the causal agent of an infectious disease, to predict the likelihood that an individual will suffer from a genetic disease, to determine the purity of drinking water or milk, or to identify tissue samples. The desire to increase the utility and applicability of such assays is often frustrated by assay sensitivity. Hence, it would be highly desirable to develop more sensitive detection assays.

Nucleic acid detection assays may be predicated on any characteristic of the nucleic acid molecule, such as its size, sequence and, if DNA, susceptibility to digestion by restriction endonucleases. The sensitivity of such assays may be increased by altering the manner in which detection is reported or signaled to the observer. Thus, for example, assay sensitivity may be increased through the use of detectably labeled reagents. A wide variety of such labels have been used for this purpose. Detectable labels include, for example, radioactive isotopes, fluorescent labels, chemiluminescent labels, bioluminescent labels and enzyme labels.

Although the use of highly detectable labeled reagents can improve the sensitivity of nucleic acid detection assays, the sensitivity of such assays remains limited by factors including, but not limited to, non-specific reactions which increase the background signal and limitations in discriminating between sequences which differ by one or a few nucleotides. In response to these problems, a variety of detection and quantification methods using DNA amplification have been developed.

Amplification of DNA by the polymerase chain reaction (PCR) uses a pair of primers whose sequences determine the specificity of the amplification. However, the amplicon sequence outside of the priming regions has little or no contribution to amplification specificity. In a typical PCR reaction, forward and reverse primers are used to preferentially target and amplify a DNA sequence of interest. In TaqMan® assays, a probe picked from within the amplicon sequence is also provided to selectively detect and monitor the amplification product. The remainder of the target sequences outside of the primer and probe regions is not utilized. A need still remains to increase the specificity of amplification reactions, especially for amplification of samples which differ by one or a few nucleotides. Examples of such analyses include, but are not limited to, genotyping, rare allele detection, and pre-amplification of mutant sequences.

SUMMARY

Provided herein are compositions, methods and kits for the detection of target nucleic acid molecules.

In one aspect, oligonucleotides are provided (herein termed "STAR (Target-Specific Amplification Restriction) primers" or "*-primers") that comprise (i) a sequence tag herein termed a "STAR tag sequence" and (ii) a sequence which hybridizes with the target nucleic acid and from which the primer is extended, copying the target nucleic acid, in the generation of an extension product. The STAR tag sequence is complementary to a portion of the extension product 3' of the STAR primer, the complementary portion of the extension product is herein referred to as the STAR tag target region. When a STAR primer hybridizes to a target nucleic acid and is extended, the extension product comprises the STAR tag sequence at the 5' end and the complement of the STAR tag sequence (i.e., the STAR tag target region) in the 3' region of the extension product. Thus, the STAR primer extension product can fold back to self-anneal thereby forming a stem-loop structure.

In certain embodiments, the STAR tag sequence is at or near the 5' terminus of the STAR primer. In certain embodiments, the STAR tag sequence is complementary to all or a portion of the binding site of another primer sequence that us used to amplify the extension product in an amplification reaction.

In one aspect, compositions are provided comprising a STAR primer. In certain embodiments, compositions are provided comprising a first oligonucleotide primer and a second oligonucleotide primer, wherein the first primer comprises a STAR tag sequence which is the same as all or a portion of the target nucleic acid hybridization sequence of the second primer. In certain embodiments, the first and second primers are a pair of forward and reverse amplification primers.

In certain embodiments, a pair of forward and reverse amplification primers are provided, wherein in at least one of the pair comprises a STAR tag sequence which is the same as all or a portion of the target nucleic acid hybridization sequence of the other primer. In certain embodiments, both primers of the pair comprise a STAR tag sequence.

In one aspect, a polynucleotide extension product is provided comprising a STAR tag sequence at the 5' end and a sequence complementary to the STAR tag sequence to the 3' side of the STAR tag sequence, wherein the STAR tag sequence and the complementary sequence render the extension product capable of forming a stem-loop structure.

In another aspect, STAR primers may be used as a universal yet convenient tool for PCR specificity enhancement.

In certain embodiments, methods are provided for inhibiting or substantially reducing undesired amplification of a target nucleic acid, comprising contacting the target nucleic acid with one or more STAR primers, wherein the STAR primer comprises a 5' STAR tag sequence, and extending the STAR primer to form an extension product, whereby the extension product inhibits or substantially reduces undesired amplification of the target nucleic acid.

In certain embodiments, methods are provided for detecting one or more target nucleic acid molecules, the methods comprising hybridizing the one or more target nucleic acid molecules with one or more STAR primers, wherein the STAR primer comprises a 5' STAR tag sequence, extending the STAR primer to form one or more extension products, amplifying the extension product(s) to form one or more amplification products, and detecting the presence or absence of at least one amplification product, thereby detecting the one or more target nucleic acid molecules.

In certain embodiments, methods are provided for detecting one or more target nucleic acid molecules, the methods comprising hybridizing the one or more target nucleic acid molecules with one or more STAR primers, wherein the STAR primer comprises a 5' STAR tag sequence, extending the STAR primer to form one or more extension products; amplifying the extension product(s) to form one or more amplification products in the presence of a detector probe, wherein the detector probe comprises at least one nucleotide of the STAR primer; and detecting the presence or absence of at least one amplification product, thereby detecting the one or more target nucleic acid molecules.

In certain embodiments, methods are provided for distinguishing between methylated and non-methylated target nucleic acids. In certain embodiments, methods are provided for detecting two or more different target nucleic acids from a single hybridization reaction. In certain embodiments, methods are provided for distinguishing two different alleles in a target nucleic acid sample.

In certain embodiments, compositions are provided, wherein the composition comprises one or more nucleic acid molecules and at least one oligonucleotide, wherein the oligonucleotide comprises a STAR tag sequence and wherein the oligonucleotide is an oligonucleotide of the present disclosure. In certain embodiments, the composition further comprises a nucleic acid polymerase. In certain embodiments, the composition further comprises a forward or reverse primer. In certain embodiments, the composition further comprises a detector probe.

In certain embodiments, kits are provided that may be used to carry out hybridization, extension and amplification reactions using the oligonucleotides described herein. In certain embodiments, kits are provided for the detection or measurement of nucleic acid synthesis or amplification products comprising one or more oligonucleotides disclosed herein, including STAR primers.

These and other features of the present teachings are provided herein.

BRIEF DESCRIPTION OF THE DRAWINGS

FIG. 2 schematically depicts alternative designs and applications of STAR primers.

DETAILED DESCRIPTION

Figure 1:
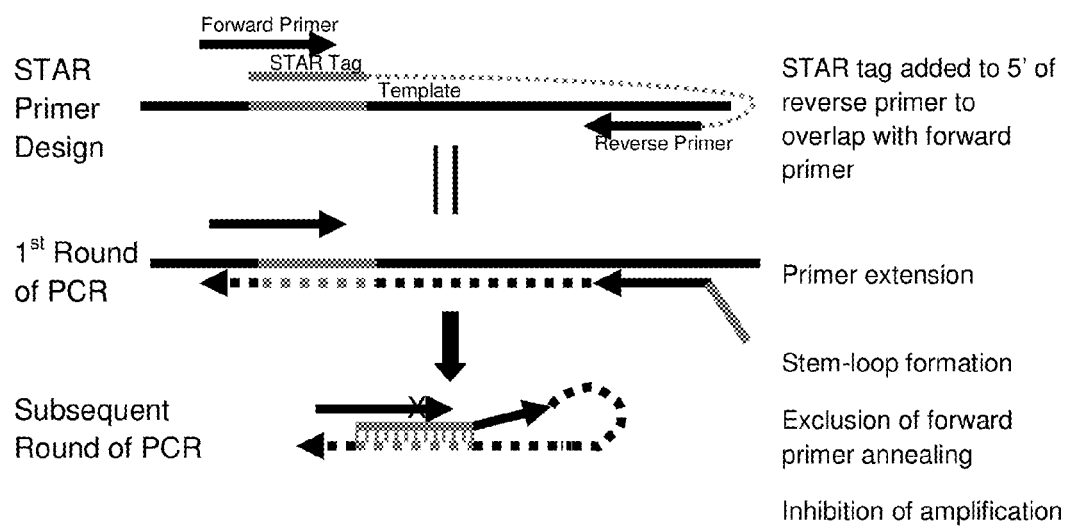
FIG. 1 schematically depicts the design of STAR primers according to certain embodiments disclosed herein.

Provided herein are compositions, methods and kits for the detection of target nucleic acids.

Amplification of DNA by PCR requires a pair of primers whose sequences determine the specificity of the amplification. However, the amplicon sequence outside of the priming regions typically is not used in the construction of primer or probe sequences. When the primer specificity is limited, especially when a desired target and unwanted target differ only in their internal sequences, both can be amplified by the same pair of primers. Therefore, internal amplicon sequences need to be utilized for further discrimination. To this end, Sequence-Targeted Amplification Restrictive (STAR) primers, disclosed herein, were designed and tested to selectively amplify the desired target while simultaneously suppressing the formation of the unwanted amplification product.

A STAR primer oligonucleotide (also referred to as "*-primer") comprises (i) a portion with a STAR tag sequence and (ii) a portion with a sequence which hybridizes with the target nucleic acid and from which the primer is extended, copying the target nucleic acid, in the generation of an extension product. The STAR tag sequence is complementary to a portion of the extension product 3' of the STAR primer, the complementary portion of the extension product is herein referred to as the STAR tag target region. When a STAR primer hybridizes to a target nucleic acid and is extended, the extension product comprises the STAR tag sequence at the 5' end and the complement of the STAR tag sequence (i.e., the STAR tag target region) in the 3' region of the extension product. Thus, the STAR primer extension product can fold back to self-anneal thereby forming a stem-loop structure. The STAR primer is designed to have a 5' STAR tag sequence capable of forming a stem-loop structure in the extension product and the STAR tag sequence may be designed against a primer region, probe region, or any amplicon internal sequence of the extension product, providing superior design flexibility for challenging applications.

In certain embodiments, the STAR tag sequence is at or near the 5' end of the STAR primer. In certain embodiments, the STAR tag sequence does not overlap with the target extension recognition sequence of the STAR primer. In certain embodiments, the STAR tag sequence partially, but not completely, overlaps with the target extension recognition sequence of the STAR primer. The target extension recognition sequence refers to the portion of the STAR primer which hybridizes to the target nucleic acid and from which the primer is extended to form an extension product. In certain embodiments, the target extension recognition sequence is specific for the target nucleic acid. In certain embodiments, the target extension recognition sequence is directed to a universal sequence, for example, in a common adaptor ligated to the end of the target nucleic acid. In certain embodiments, the target extension recognition sequence comprises a poly (T) sequence to hybridize, for example, to a polyadenylated target nucleic acid.

In certain embodiments, the STAR tag sequence is complementary to all or a portion of the binding site of another primer sequence that is used to amplify the extension product in an amplification reaction (see, for example, FIG. 1). When the STAR primer is extended, the extension product may fold back upon itself thereby forming a stem-loop structure between the STAR tag sequence at the 5' end of the extension product and the complement of the STAR tag sequence in the 3' region of the extension product. The stem-loop structure formed by the STAR primer extension product excludes annealing of the other primer used to amplify the target molecule, thereby inhibiting amplification of the unwanted target.

In certain embodiments, the STAR tag sequence is complementary to a portion of the amplicons internal sequence. In certain embodiments, the STAR tag sequence is complementary to a portion of the internal amplicon sequence and to the binding site of another primer sequence. The stem-loop structure formed by the extension product of such a STAR primer blocks annealing of another primer or the extension by a DNA polymerase, thereby blocking any further amplification of the extension product.

In certain embodiments, the forward primer in an amplification reaction is a STAR primer. In certain embodiments, the reverse primer in an amplification reaction is a STAR primer. In certain embodiments, both the forward and reverse primers in an amplification reaction are STAR primers.

In certain embodiments, a STAR primer is provided comprising a STAR tag sequence which is the same as sequence a sequence in the nucleic acid to which the STAR primer is targeted. For example, in some embodiments, the STAR primer comprises a STAR tag sequence which is the same as a primer hybridization sequence in the targeted nucleic acid. In certain embodiments, the STAR primer comprises a STAR tag sequence which is the same as a portion of the targeted nucleic acid which is 3' of a primer hybridization sequence in the targeted nucleic acid. In certain embodiments, the STAR primer comprises a STAR tag sequence which is the same as all or a portion of a primer hybridization sequence and a portion of the targeted nucleic acid which is 3' of a primer hybridization sequence in the targeted nucleic acid. In such embodiments, an extension product, formed by extension of the STAR primer hybridized to the target nucleic acid past the other primer hybridization sequence of the target nucleic acid, has two complementary sequence portions which allow the extension product to form a stem-loop structure.

In a certain embodiments, a polynucleotide extension product is provided comprising a STAR primer at the 5' end and a sequence complementary to the STAR tag sequence of the STAR primer 3' of the STAR primer such that the extension product is capable of forming a stem-loop structure using the complementary sequences. In certain embodiments, a STAR primer-based extension product is capable of forming a stem-loop structure at PCR extension temperatures. In certain embodiments, a STAR primer-based extension product in the stem-loop structure excludes annealing of a different primer to the extension product.

Figure 2A:
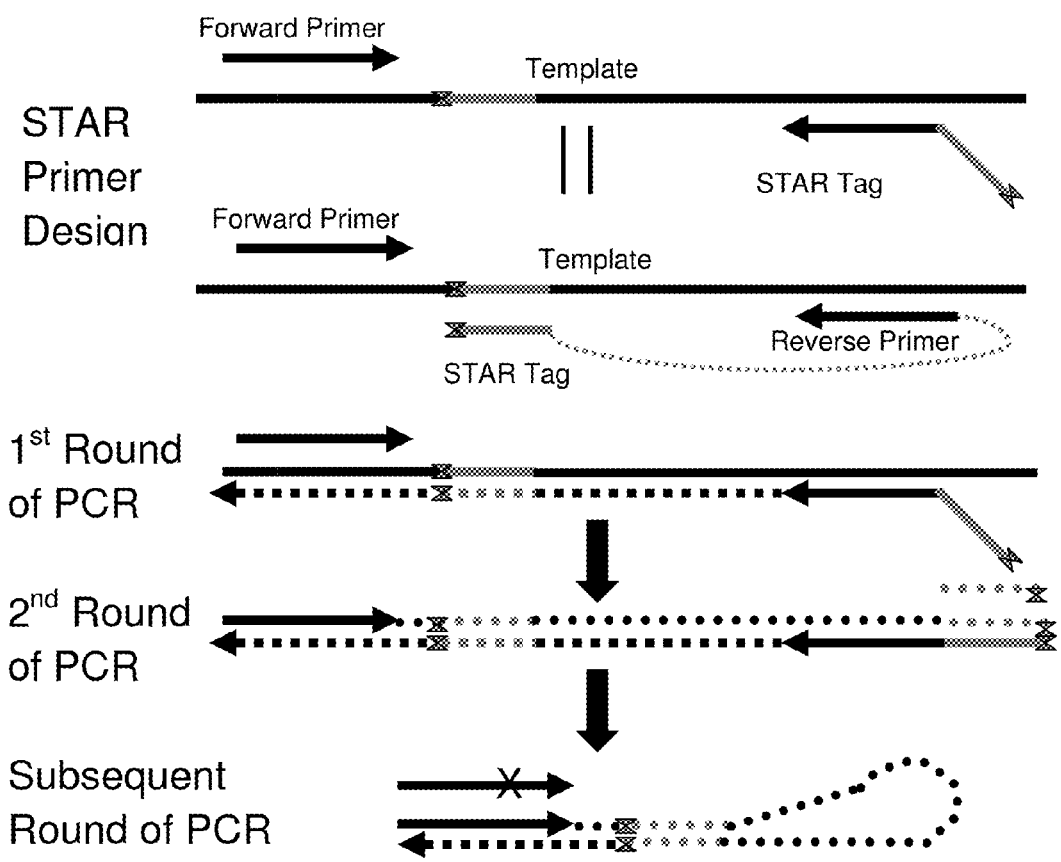
FIG. 2A depicts alternative STAR primer design.

In certain embodiments, a STAR primer may be designed to comprise a 5' STAR tag sequence that may form a stem-loop structure at PCR extension temperatures once the primer is extended (see FIG. 2A). The STAR tag sequence may be selected to completely or partially overlap with another primer to be used in amplification of the target molecule to exclude the annealing of the other primer. Without wishing to be bound by a particular theory, it appears that the formation of the stem-loop is faster than the annealing of the primer to the target molecule and the stem-loop structure is more stable due to favorable entropy. Thus, the STAR primer effectively prevents the annealing and extension of the other primer, leading to much reduced PCR efficiency.

In certain embodiments, STAR primer oligonucleotides are provided wherein the STAR tag sequence is designed to loop back and be extended in PCR (see, for example, FIG. 2A). In certain embodiments, the 5' most sequence in the STAR primer is designed in the same strand of the priming domain to target particular sequences contained within the amplicons (See "x" in the primer and amplicon in FIG. 2A). The sequence may be extended from another primer in the second round of PCR whereby it folds back and self replicates the 5' sequence when perfectly matched, thereby making the extension product inaccessible to amplification. The 5' end of the STAR primer can be designed to be the same as the target to suppress the amplification. Target nucleic acids with mismatches to the STAR tag sequence are amplified normally.

In certain embodiments, a composition is provided comprising a first and a second primer where the first primer comprises a STAR tag sequence which is the same as all or a portion of the target binding sequence of the second primer. In certain embodiments, the same sequence shared between the first and second primers in the composition is between 3 and 15 nucleotides in length. In certain embodiments, the shared sequence is 3, 4, 5, 6, 7, 8, 9, 10, 11, 12, 13, 14, or 15 nucleotides in length.

In certain embodiments, a pair of amplification primers are provided wherein in at least one of the primers comprises a STAR tag sequence, wherein the STAR tag sequence comprises all of a portion of the target binding sequence of the other primer. In certain embodiments, the primer comprising the STAR tag sequence is a forward primer and the other primer is a reverse primer. In certain embodiments, the primer comprising the STAR tag sequence is a reverse primer and the other primer is a forward primer. In certain embodiments, both primers of the pair of amplification primers comprise a STAR tag sequence.

In certain embodiments, the STAR primer length is between about 20-60 nucleotides. In certain embodiments, the STAR primer is about 20 to about 50 nucleotides in length. In certain embodiments, the STAR primer is about 20 to about 45, about 25 to about 50, about 25 to about 45, or about 30 to about 40 nucleotides in length. In certain embodiments, the STAR primer is about 30, 31, 32, 33, 34, 35, 36, 37, 38, 39, 40, 41, 42, 43, 44, or 45 nucleotides in length.

In certain embodiments, the STAR tag sequence is about 10 to about 40 nucleotides in length. In certain embodiments, the STAR tag sequence length is between about 30-35 nucleotides. In certain embodiments, the STAR tag sequence is about 10 to about 30, about 10 to about 35, about 10 to about 20, about 15 to about 30, about 15 to about 25, about 20 to about 40, about 20 to about 25, or about 30 to about 40 nucleotides in length.

In certain embodiments, the STAR primer is a forward primer. In certain embodiments, the STAR primer is a reverse primer. In certain embodiments, the STAR tag sequence is completely contained within the second primer binding region. In certain embodiments, the STAR tag sequence is completely contained within the target sequence downstream of the second primer binding region (i.e., in the region of the target nucleic acid to be amplified). In certain embodiments, the STAR tag sequence bridges the second primer binding region and the target nucleic acid to be amplified. In certain embodiments, the overlap of the STAR tag sequence with the second primer binding region may be 0, 1, 2, 3, 4, 5, 6, 7, 8, 9, 10, 11, 12 or 13 nucleotides. Preferably, this overlap is 11, 12, or 13 nucleotides. In particular embodiments, the overlap of the STAR tag sequence with the second primer binding region is 12 nucleotides. In certain embodiments, the overlap of the STAR tag sequence with the target sequence downstream of the second primer binding region may be 0, 1, 2, 3, 4, 5, 6, 7, 8, 9, 10, 11, 12 or 13 nucleotides. Preferably, this overlap is 11, 12, or 13 nucleotides. In particular embodiments, the overlap of the STAR tag sequence with the the target sequence downstream of the second primer binding region is 12 nucleotides. In certain embodiments, the STAR tag sequence is a perfect match with the target nucleic acid. In certain embodiments, the STAR tag sequence contains a mismatch with the target nucleic acid.

In certain embodiments, STAR primers may be used as a universal yet convenient tool for PCR specificity enhancement. STAR primers may be widely applicable to use in genotyping, single nucleotide polymorphism (SNP) detection, rare allele detection, pre-amplification of mutant sequences, rare mutant detection, DNA methylation analysis, selective suppression of unwanted background DNA, library subtraction, and the like. In addition, STAR primers may be used for selective amplification suppression of ligated ligation adaptors in the pre-amplification of adaptor-ligated miRNA and TaqMan® assay distinction of homologous miRNA (see, co-owned, co-pending U.S. Provisional Patent Application No. 61/721,968, filed Nov. 2, 2012, and PCT Application No. PCT/US2013/068350, entitled "Small RNA Capture, Detection and Quantification," filed concurrently herewith, each of which are herein incorporated by reference in its entirety.

In certain embodiments, methods are provided for inhibiting or substantially reducing undesired amplification of a target nucleic acid, comprising contacting the target nucleic acid with one or more STAR primers, wherein the STAR primer comprises a 5' STAR tag sequence, and extending the STAR primer to form an extension product, whereby the extension product inhibits or substantially reduces undesired amplification of the target nucleic acid.

In certain embodiments, methods are provided for detecting one or more target nucleic acid molecules, the methods comprising hybridizing the one or more target nucleic acid molecules with one or more STAR primers, wherein the STAR primer comprises a 5' STAR tag sequence, extending the STAR primer to form one or more extension products, amplifying the extension product(s) to form one or more amplification products, and detecting the presence or absence of at least one amplification product, thereby detecting the one or more target nucleic acid molecules.

In certain embodiments, methods are provided for detecting one or more target nucleic acid molecules, the methods comprising hybridizing the one or more target nucleic acid molecules with one or more STAR primers, wherein the STAR primer comprises a 5' STAR tag sequence, extending the STAR primer to form one or more extension products; amplifying the extension product(s) to form one or more amplification products in the presence of a detector probe, wherein the detector probe comprises at least one nucleotide of the STAR primer; and detecting the presence or absence of at least one amplification product, thereby detecting the one or more target nucleic acid molecules.

In certain embodiments, methods are provided for detecting two or more different target nucleic acid molecules from a single hybridization reaction, comprising hybridizing a first STAR primer and a first target nucleic acid, and a second STAR primer and a second target nucleic acid, wherein the first STAR primer hybridizes to the first target nucleic acid and the second STAR primer hybridizes to the second target nucleic acid; extending the first STAR primer and the second STAR primer to form extension products; dividing the extension products into a first amplification reaction to form a first amplification product and a second amplification reaction to form a second amplification product, wherein a primer in the first amplification reaction corresponds to the first target nucleic acid and not the second target nucleic acid and a primer in the second amplification reaction corresponds to the second target nucleic acid and not the first nucleic acid, wherein a first detector probe in the first amplification reaction differs from a second detector probe in the second amplification reaction, wherein the first detector probe comprises at least one nucleotide of the first STAR primer and the second detector probe comprises at least one nucleotide of the second STAR primer; and detecting the two different target nucleic acids.

Figure 2B:
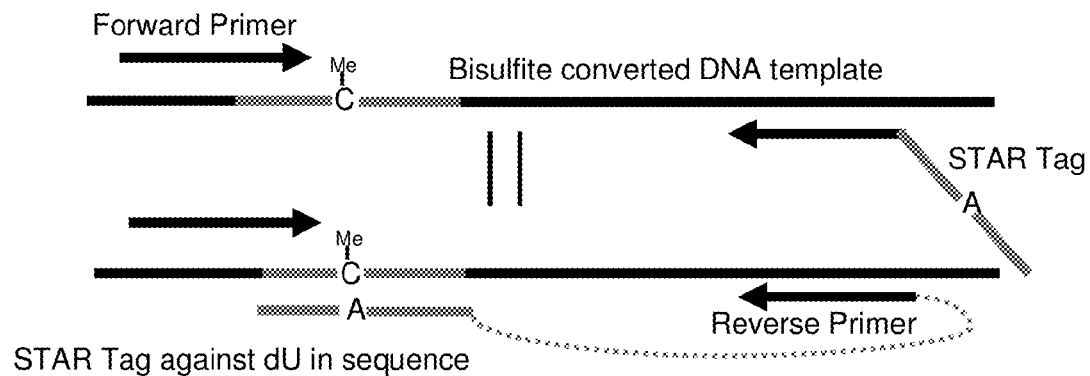
FIG. 2B depicts use of a STAR primer in methylation detection.
Figure 2B:
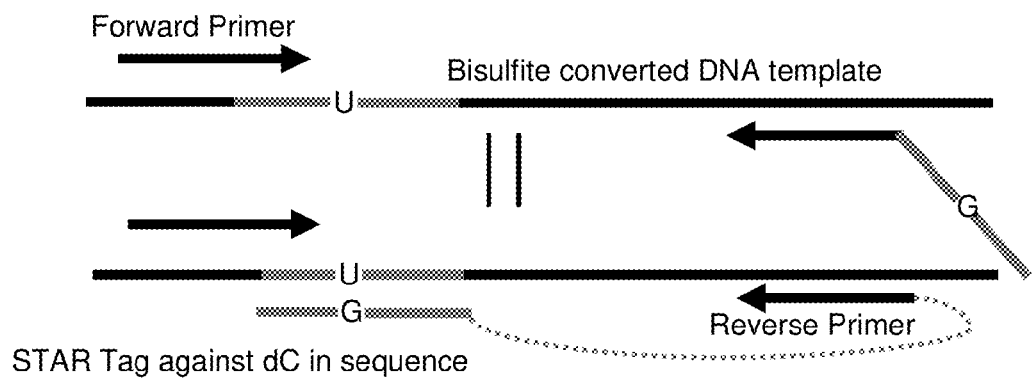
Figure 2C:
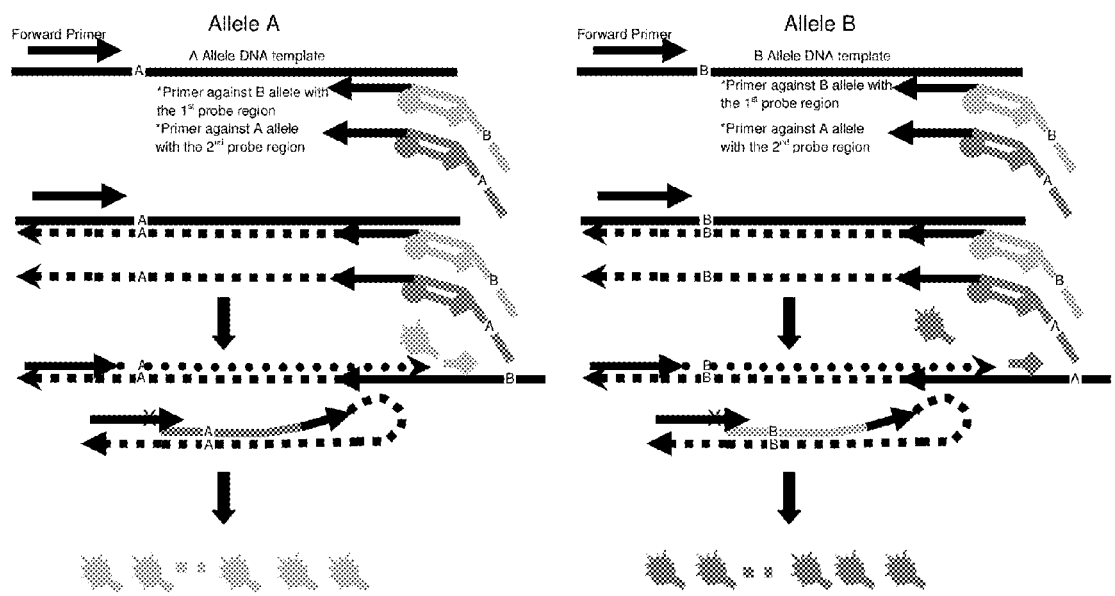
FIG. 2C depicts genotyping with generic probes using STAR primers.

In certain embodiments, methods are provided for distinguishing two different alleles in a target nucleic acid, comprising combining said target nucleic acid with a first STAR primer and a second STAR primer, wherein said first STAR primer comprises a STAR tag sequence corresponding to a first allele, and the second STAR primer comprising a STAR tag sequence corresponding to a second allele, and a common reverse or forward primer which hybridizes to said target nucleic acid; extending the first and second STAR primers to form a first and second extension product, respectively; amplifying the first and second extension products to form first and second amplification products, respectively; and detecting the presence or absence of the first and second amplification products, wherein the presence of the first amplification product indicates the presence of the second allele and the presence of the second amplification product indicates the presence of the first allele. For example, STAR primer designs may be used for genotyping analysis with a pair of generic TaqMan® probes that are incorporated into the STAR primers (see FIG. 2C).

For example, a reaction is used to amplify a particular locus in a nucleic acid sample with two STAR primers, one with a STAR tag sequence complementary to a first allele of the locus and the other with a STAR tag sequence complementary to a second allele of the locus, and a common reverse or forward primer which hybridizes to the locus target nucleic acid; extending the STAR primers to form extension products; amplifying the extension products to form amplification products; and detecting the presence or absence of the amplification products. Labeled detector probes, such as TaqMan probes, that hybridize with the STAR primers may be used. In certain embodiments, the detector probes differ for the first and the second STAR primers. For example, a detector probe labeled with one dye is used with the first STAR primer and a detector probe labeled with a different dye is used with the second STAR primer.

When the first allele is present in nucleic acid sample, the use of a STAR primer with a STAR tag sequence designed to be complementary to the first allele sequence will result in an extension product in which the STAR tag sequence and tag target region are complementary, allowing the extension product to fold back to self-anneal into a stem-loop structure. Thus, amplification of the extension product comprising the first allele is suppressed and the amount of amplification product is greatly reduced or absent. The STAR primer with the STAR tag sequence designed to be complementary to the second allele sequence will result in an extension product in which the STAR tag sequence and tag target region are mismatched. With this mismatch, the extension product comprising the second allele does not self-anneal, or at least not to a sufficient extent, so as not to suppress amplification. Thus, absence of the amplification product from the STAR primer directed to the first allele ("the first allele amplification product") and presence of the amplification product from the STAR primer directed to the second allele ("the second allele amplification product") indicates the presence of the first allele in the target nucleic acid sample. Presence of the first allele amplification product and absence of the second allele amplification product indicates the presence of the second allele in the target nucleic acid sample.

In certain embodiments, methods are provided for distinguishing between methylated and non-methylated target nucleic acids. Using bisulfite converted genomic DNA, STAR primers may be used to quantitate DNA methylation. See, for example, FIG. 2B. The STAR primers may be designed for suppression of methylated DNA amplification by targeting against dC in the target nucleic acid, or for suppression of non-methylated DNA amplification by targeting against dU in the target nucleic acid.

For example, a reaction is used to amplify bisulfite treated target nucleic acid with a STAR primer, wherein said STAR primer comprises a STAR tag sequence corresponding to non-methylated STAR tag target sequences in the target nucleic acid, and a common reverse or forward primer which hybridizes to said target nucleic acid; extending the STAR primer to form a extension product; amplifying the extension products to form amplification products; and detecting the presence or absence of the amplification products, wherein the presence of the amplification product indicates the presence of methylation and the absence of the amplification product indicates the absence of the methylation.

Bisulfite treatment converts non-methylated cytosines to uracil and does not change methylated cytosines. When the target nucleic acid is non-methylated at the nucleotide base being interrogated for its methylation status, the use of a STAR primer with a STAR tag sequence designed to be complementary to a non-methylated target sequence (for example, a STAR tag sequence comprising an "A" to be complementary to a converted dU in the STAR tag target region at the interrogated nucleotide base) will result in an extension product in which the STAR tag sequence and tag target region are complementary, allowing the extension product to fold back to self-anneal into a stem-loop structure. Thus, amplification of the extension product is suppressed and the amount of amplification product is greatly reduced or absent, thereby indicating absence of methylation in the target nucleic acid. When the target nucleic acid is methylated at the nucleotide base being interrogated for its methylation status, the use of the STAR primer with the STAR tag sequence directed to the non-methylated target sequence will result in an extension product in which the STAR tag sequence and tag target region are mismatched (the "A" of the STAR tag sequence and the "C" of the STAR tag target region). With this mismatch, the extension product does not self-anneal, or at least not to a sufficient extent, so as not to suppress amplification. Thus, the presence of the amplification product indicates methylation in the target nucleic acid.

In another embodiment, a similar reaction is used to amplify DNA with a STAR primer comprising a methylated DNA-specific STAR tag sequence. The use of a STAR primer with a STAR tag sequence designed to be complementary to a methylated target sequence (for example, a STAR tag sequence comprising an "G" to be complementary to a dC in the STAR tag target region at the nucleotide base being interrogated for methylation) will result in an extension product in which the STAR tag sequence and tag target region are complementary when the target DNA is methylated. This complementarity allows the extension product to fold back and self-anneal into a stem-loop structure. Thus, amplification of the extension product is suppressed and the amount of amplification product is greatly reduced or absent, thereby indicating presence of methylation in the target nucleic acid. When the target nucleic acid is non-methylated at the nucleotide base being interrogated for its methylation status, the use of the STAR primer with the STAR tag sequence directed to the methylated target sequence will result in an extension product in which the STAR tag sequence and tag target region are mismatched (the "G" of the STAR tag sequence and the "U" of the STAR tag target region). With this mismatch, the extension product does not self-anneal, or at least not to a sufficient extent, so as not to suppress amplification. Thus, the presence of the amplification product indicates non-methylation in the target nucleic acid.

In another embodiment, the two reactions are combined for quantitation of DNA methylation.

In certain embodiments, compositions are provided, wherein the composition comprises one or more nucleic acid molecules and at least one oligonucleotide, wherein the oligonucleotide comprises a STAR tag sequence and wherein the oligonucleotide is an oligonucleotide of the present disclosure. In certain embodiments, the composition further comprises a nucleic acid polymerase. In certain embodiments, the composition further comprises a forward or reverse primer. In certain embodiments, the composition further comprises a detector probe.

In certain embodiments, kits are provided that may be used to carry out hybridization, extension and amplification reactions using the oligonucleotides described herein. Preferred kits may comprise one or more containers (such as vials, tubes, and the like) configured to contain the reagents used in the methods described herein and optionally may contain instructions or protocols for using such reagents. The kits described herein may comprise one or more components selected from the group consisting of one or more oligonucleotides described herein (including, but not limited to STAR primers, forward and reverse primers, and detector probes), one or more DNA polymerase, such as a thermostable polymerase, one or more reverse transcriptases, or any other DNA or RNA polymerase, one or more agents capable of quenching one or more of the labels, one or more buffers or buffering salts, one or more nucleotides, one or more target/template molecules (which may be used for determining reaction performance, i.e., control reactions) and other reagents for analysis or further manipulation of the products or intermediates produced by the methods described herein. Such additional components may include components used for cloning and/or sequencing and components or equipment needed for the detection or quantification of the nucleic acid molecule of interest.

In certain embodiments, kits are further provided for use in synthesis of a nucleic acid molecule, said kit comprising one or more oligonucleotides disclosed herein, including STAR primers. In certain embodiments, kits are provided for use in amplification of a nucleic acid molecule, said kit comprising one or more oligonucleotides disclosed herein, including STAR primers. In certain embodiments, kits are provided for the detection or measurement of nucleic acid synthesis or amplification products comprising one or more oligonucleotides disclosed herein, including STAR primers.

To more clearly and concisely describe and point out the subject matter of the present disclosure, the following definitions are provided for specific terms, which are used in the following description and the appended claims. Throughout the specification, exemplification of specific terms should be considered as non-limiting examples.

As used in this specification, the words "a" or "an" means at least one, unless specifically stated otherwise. In this specification, the use of the singular includes the plural unless specifically stated otherwise. For example, but not as a limitation, "a target nucleic acid" means that more than one target nucleic acid can be present; for example, one or more copies of a particular target nucleic acid species, as well as two or more different species of target nucleic acid. The term "and/or" means that the terms before and after the slash can be taken together or separately. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. All literature cited in the specification, including but not limited to, patent, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The terms "amplicon" and "amplification product" as used herein generally refer to the product of an amplification reaction. An amplicon may be double-stranded or single-stranded, and may include the separated component strands obtained by denaturing a double-stranded amplification product. In certain embodiments, the amplicon of one amplification cycle can serve as a template in a subsequent amplification cycle.

The terms "annealing" and "hybridizing", including, without limitation, variations of the root words "hybridize" and "anneal", are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in *Nucleic Acid Hybridization, A Practical Approach*, Hames and Higgins, eds., IRL Press, Washington, D.C. (1985) and Wetmur and Davidson, *Mol. Biol.* 31:349 (1968).

In general, whether such annealing takes place is influenced by, among other things, the length of the complementary portions of the complementary portions of the primers and their corresponding binding sites in the target flanking sequences and/or amplicons, or the corresponding complementary portions of a reporter probe and its binding site; the pH; the temperature; the presence of mono- and divalent cations; the proportion of G and C nucleotides in the hybridizing region; the viscosity of the medium; and the presence of denaturants. Such variables influence the time required for hybridization. Thus, the preferred annealing conditions will depend upon the particular application. Such conditions, however, can be routinely determined by persons of ordinary skill in the art, without undue experimentation. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature.

The term "selectively hybridize" and variations thereof, means that, under appropriate stringency conditions, a given sequence (for example, but not limited to, a primer) anneals with a second sequence comprising a complementary string of nucleotides (for example, but not limited to, a target flanking sequence or primer binding site of an amplicon), but does not anneal to undesired sequences, such as non-target nucleic acids, probes, or other primers. Typically, as the reaction temperature increases toward the melting temperature of a particular double-stranded sequence, the relative amount of selective hybridization generally increases and mis-priming generally decreases. In this specification, a statement that one sequence hybridizes or selectively hybridizes with another sequence encompasses situations where the entirety of both of the sequences hybridize or selectively hybridize to one another, and situations where only a portion of one or both of the sequences hybridizes or selectively hybridizes to the entire other sequence or to a portion of the other sequence.

As used herein, the term "stringency" is used to define the temperature and solvent composition existing during hybridization and the subsequent processing steps at which a hybrid comprised of two complementary nucleotide sequences will form. Stringency also defines the amount of homology, the conditions necessary, and the stability of hybrids formed between two nucleotide sequences. As the stringency conditions increase, selective hybridization is favored and non-specific cross-hybridization is disfavored. Increased stringency conditions typically correspond to higher incubation temperature, lower salt concentrations, and/or higher pH, relative to lower stringency conditions at which mis-priming is more likely to occur. Those in the art understand that appropriate stringency conditions to enable the selective hybridization of a primer or primer pair to a corresponding target flanking sequence and/or amplicon can be routinely determined using well known techniques and without undue experimentation (see, e.g., *PCR: The Basics from Background to Bench*, McPherson and Moller, Bios Scientific Publishers, 2000).

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The terms "denaturing" and "denaturation" as used herein refer to any process in which a double-stranded polynucleotide, including without limitation, a genomic DNA (gDNA) fragment comprising at least one target nucleic acid, a double-stranded amplicon, or a polynucleotide comprising at least one double-stranded segment is converted to two single-stranded polynucleotides or to a single-stranded or substantially single-stranded polynucleotide, as appropriate. Denaturing a double-stranded polynucleotide includes, without limitation, a variety of thermal and chemical techniques which render a double-stranded nucleic acid single-stranded or substantially single-stranded, for example but not limited to, releasing the two individual single-stranded components of a double-stranded polynucleotide or a duplex comprising two oligonucleotides. Those in the art will appreciate that the denaturing technique employed is generally not limiting unless it substantially interferes with a subsequent annealing or enzymatic step of an amplification reaction, or in certain methods, the detection of a fluorescent signal.

As used herein, the term "Tm" is used in reference to melting temperature. The melting temperature is the temperature at which a population of double-stranded nucleic acid molecules becomes half dissociated into single strands.

The term "minor groove binder" as used herein refers to a small molecule that fits into the minor groove of double-stranded DNA, sometimes in a sequence specific manner. Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example, but not limited to, furan, benzene, or pyrrole rings.

The term "end-point" measurement refers to a method where data collection occurs only once the reaction has been stopped.

The terms "real-time" and "real-time continuous" are interchangeable and refer to a method where data collection occurs through periodic monitoring during the course of the polymerization reaction. Thus, the methods combine amplification and detection into a single step.

As used herein, the term "quantitative PCR" refers to the use of PCR to quantify gene expression.

As used herein the terms "$C_t$" and "cycle threshold" refer to the time at which fluorescence intensity is greater than background fluorescence. They are characterized by the point in time (or PCR cycle) where the target amplification is first detected. Consequently, the greater the quantity of target DNA in the starting material, the faster a significant increase in fluorescent signal will appear, yielding a lower $C_t$.

As used herein, the term "primer" refers to a synthetically or biologically produced single-stranded oligonucleotide that is extended by covalent bonding of nucleotide monomers during amplification or polymerization of a nucleic acid molecule. Nucleic acid amplification often is based on nucleic acid synthesis by a nucleic acid polymerase or reverse transcriptase. Many such polymerases or reverse transcriptases require the presence of a primer that may be extended to initiate such nucleic acid synthesis. A primer is typically 11 bases or longer; most preferably, a primer is 17 bases or longer, although shorter or longer primers may be used depending on the need. As will be appreciated by those skilled in the art, the oligonucleotides disclosed herein may be used as one or more primers in various extension, synthesis, or amplification reactions.

The terms "complementarity" and "complementary" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementarity refers to the situation in which each nucleotide unit of one polynucleotide strand or region can hydrogen bond with each nucleotide unit of a second polynucleotide strand or region. "Less than perfect complementarity" refers to the situation in which some, but not all, nucleotide units of two strands or two units can hydrogen bond with each other.

As used herein, the term "reverse complement" refers to a sequence that will anneal/base pair or substantially anneal/base pair to a second oligonucleotide according to the rules defined by Watson-Crick base pairing and the antiparallel nature of the DNA-DNA, RNA-RNA, and RNA-DNA double helices. Thus, as an example, the reverse complement of the RNA sequence 5'-AAUUUGC would be 5'-GCAAAUU. Alternative base pairing schemes, including but not limited to G-U pairing, can also be included in reverse complements.

As used herein, the term "probe" refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences.

As used herein, "substantially less extendable" is used to characterize an oligonucleotide that is inefficiently extended or not extended in an extension and/or amplification reaction when the 3' most nucleotide of the oligonucleotide is not complementary to the corresponding base of a target/template nucleic acid.

As used herein, the term "template" is interchangeable with "target molecule" or "target nucleic acid" and refers to a double-stranded or single-stranded nucleic acid molecule which is to be amplified, copied or extended, synthesized, or sequenced. In the case of a double-stranded DNA molecule, denaturation of its strands to form a first and a second strand is performed to amplify, sequence, or synthesize these molecules. A primer, complementary to a portion of a template is hybridized under appropriate conditions and the polymerase (DNA polymerase or reverse transcriptase) may then synthesize a nucleic acid molecule complementary to said template or a portion thereof. The newly synthesized molecule, according to the present disclosure, may be equal or shorter in length than the original template. Mismatch incorporation during the synthesis or extension of the newly synthesized molecule may result in one or a number of mismatched base pairs. Thus, the synthesized molecule need not be exactly complementary to the template. The template may be an RNA molecule, a DNA molecule, or a DNA/RNA hybrid molecule. A newly synthesized molecule may serve as a template for subsequent nucleic acid synthesis or amplification.

As used herein, the term "extension reaction" refers to an elongation reaction in which a primer hybridized to a target nucleic acid is extended to form an "extension product" comprising a strand complementary to the target nucleic acid.

The target nucleic acid may be obtained from any source, and may comprise any number of different compositional components. For example, the target may be a nucleic acid (e.g., DNA or RNA), transfer RNA (tRNA), small interfering RNA (siRNA), microRNA (miRNA), or other mature small RNA, and may comprise nucleic acid analogs or other nucleic acid mimics. The target may be methylated, non-methylated, or both. The target may be bisulfite-treated and non-methylated cytosines converted to uracil. Further, it will be appreciated that "target nucleic acid" may refer to the target nucleic acid itself, as well as surrogates thereof, for example, amplification products and native sequences. The target molecules of the present teachings may be derived from any number of sources, including without limitation, viruses, archae, protists, prokaryotes and eukaryotes, for example, but not limited to, plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells and lysed cells. It will be appreciated that target nucleic acids may be isolated from samples using any of a variety of procedures known in the art, for example, the Applied Biosystems ABI Prism® 6100 Nucleic Acid PrepStation (Life Technologies Corp., Carlsbad, Calif.) and the ABI Prism® 6700 Automated Nucleic Acid Workstation (Life Technologies Corp.), Ambion® mirVana™ RNA isolation kit (Life Technologies Corp.), and the like. It will be appreciated that target nucleic acids may be cut or sheared prior to analysis, including the use of such procedures as mechanical force, sonication, restriction endonuclease cleavage, or any method known in the art. In general, the target nucleic acids of the present teachings will be single-stranded, though in some embodiments the target nucleic acids may be double-stranded, and a single-strand may result from denaturation.

As used herein, the terms "hairpin" and "stem-loop" are interchangeable and are used to indicate the structure of an oligonucleotide in which one or more portions of the oligonucleotide form base pairs with one or more other portions of the oligonucleotide. When the two portions are base paired to form a double-stranded portion of the oligonucleotide, the double-stranded portion may be referred to as a stem. Thus, depending on the number of complementary portions used, a number of stems (preferably about 1 to about 10) may be formed.

The term "incorporating" as used herein, means becoming a part of a DNA or RNA molecule or primer.

The term "nucleic acid binding dye" as used herein refers to a fluorescent molecule that is specific for a double-stranded polynucleotide or that at least shows a substantially greater fluorescent enhancement when associated with double-stranded polynucleotides than with a single stranded polynucleotide. Typically, nucleic acid binding dye molecules associate with double-stranded segments of polynucleotides by intercalating between the base pairs of the double-stranded segment, but binding in the major or minor grooves of the double-stranded segment, or both. Non-limiting examples of nucleic acid binding dyes include ethidium bromide, DAPI, Hoechst derivatives including without limitation Hoechst 33258 and Hoechst 33342, intercalators comprising a lanthanide chelate (for example, but not limited to, a naphthalene diimide derivative carrying two fluorescent tetradentate β-diketone-$Eu^{3+}$ chelates (NDI-(BHHCT-$Eu^{3+}$)$_2$), see e.g., Nojima et al., *Nucl. Acids Res.* Suppl. No. 1 105 (2001), and certain unsymmetrical cyanine dyes such as SYBR® Green and PicoGreen®.

As used herein, the terms "polynucleotide", "oligonucleotide," and "nucleic acid" are used interchangeably and refer to single-stranded and double-stranded polymers of nucleotide monomers, including without limitation, 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and may include nucleotide analogs. The nucleotide monomer units may comprise any of the nucleotides described herein, including, but not limited to, nucleotides and/or nucleotide analogs. Polynucleotides typically range in size from a few monomeric units, e.g., 5-40 when they are sometimes referred to in the art as oligonucleotides, to several thousands of monomeric nucleotide units. Unless denoted otherwise, whenever a polynucleotide sequence is represented, it will be understood that the nucleotides are in the 5'-to-3' order from left to right and that "A" denotes deoxyadenosine, "C" denotes deoxycytosine, "G" denotes deoxyguanosine, "T" denotes deoxythymidine, and "U" denotes deoxyuridine, unless otherwise noted.

The term "nucleotide" refers to a phosphate ester of a nucleoside, e.g., triphosphate esters, wherein the most common site of esterification is the hydroxyl group attached at the C-5 position of the pentose.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine.

The term "analog" includes synthetic analogs having modified base moieties, modified sugar moieties, and/or modified phosphate ester moieties. Phosphate analogs generally comprise analogs of phosphate wherein the phosphorous atom is in the +5 oxidation state and one or more of the oxygen atoms is replaced with a non-oxygen moiety, e.g. sulfur. Exemplary phosphate analogs include: phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$. Exemplary base analogs include: 2,6-diaminopurine, hypoxanthine, pseudouridine, C-5-propyne, isocytosine, isoguanine, 2-thiopyrimidine. Exemplary sugar analogs include: 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, and bromo.

As used herein, the term "reaction vessel" generally refers to any container, chamber, device, or assembly, in which a reaction can occur in accordance with the present teachings. In some embodiments, a reaction vessel may be a microtube, for example, but not limited to, a 0.2 mL or a 0.5 mL reaction tube such as a MicroAmp® Optical tube (Life Technologies Corp., Carlsbad, Calif.) or a micro-centrifuge tube, or other containers of the sort in common practice in molecular biology laboratories. In some embodiments, a reaction vessel comprises a well of a multi-well plate, a spot on a glass slide, or a channel or chamber of a microfluidics device, including without limitation a TaqMan® Low Density Array or a TaqMan® Open Array Real-Time PCR plate (both from Life Technologies Corp.). For example, but not as a limitation, a plurality of reaction vessels can reside on the same support. In some embodiments, lab-on-a-chip-like devices available, for example, from Caliper, Fluidigm and Life Technologies Corp., including the Ion 316™ and Ion 318™ Chip, may serve as reaction vessels in the disclosed methods. It will be recognized that a variety of reaction vessels are commercially available or can be designed for use in the context of the present teachings.

The term "reporter group" is used in a broad sense herein and refers to any identifiable tag, label, or moiety.

The term "thermostable" when used in reference to an enzyme, refers to an enzyme (such as a polypeptide having nucleic acid polymerase activity) that is resistant to inactivation by heat. A "thermostable" enzyme is in contrast to a "thermolabile" polymerase, which can be inactivated by heat treatment. Thermolabile proteins can be inactivated at physiological temperatures, and can be categorized as mesothermostable (inactivation at about 45° C. to about 65° C.), and thermostable (inactivation at greater than about 65° C.). For example, the activities of the thermolabile T5 and T7 DNA polymerases can be totally inactivated by exposing the enzymes to a temperature of about 90° C. for about 30 seconds. A thermostable polymerase activity is more resistant to heat inactivation than a thermolabile polymerase. However, a thermostable polymerase does not mean to refer to an enzyme that is totally resistant to heat inactivation; thus heat treatment may reduce the polymerase activity to some extent. A thermostable polymerase typically will also have a higher optimum temperature than thermolabile DNA polymerases.

The term "working concentration" refers to the concentration of a reagent that is at or near the optimal concentration used in a solution to perform a particular function (such as amplification or digestion of a nucleic acid molecule). The working concentration of a reagent is also described equivalently as a "1× concentration" or a "1× solution" (if the reagent is in solution) of the reagent. Accordingly, higher concentrations of the reagent may also be described based on the working concentration; for example, a "2× concentration" or a "2× solution" of a reagent is defined as a concentration or solution that is twice as high as the working concentration of the reagent; a "5× concentration" or a "5× solution" is five times as high as the working concentration, and so on.

As used herein, the terms "amplification", "nucleic acid amplification", or "amplifying" refer to the production of multiple copies of a nucleic acid template, or the production of multiple nucleic acid sequence copies that are complementary to the nucleic acid template. The terms (including the term "polymerizing") may also refer to extending a nucleic acid template (e.g., by polymerization). The amplification reaction may be a polymerase-mediated extension reaction such as, for example, a polymerase chain reaction (PCR). However, any of the known amplification reactions may be suitable for use as described herein. The term "amplifying" that typically refers to an "exponential" increase in target nucleic acid may be used herein to describe both linear and exponential increases in the numbers of a select target sequence of nucleic acid.

The term "amplification reaction mixture" and/or "master mix" may refer to an aqueous solution comprising the various (some or all) reagents used to amplify a target nucleic acid. Such reactions may also be performed using solid supports (e.g., an array). The reactions may also be performed in single or multiplex format as desired by the user. These reactions typically include enzymes, aqueous buffers, salts, amplification primers, target nucleic acid, and nucleoside triphosphates. Depending upon the context, the mixture can be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, it is expected that the modified detergents describe herein should be effective in other types of nucleic acid amplification reactions, including both polymerase-mediated amplification reactions (such as helicase-dependent amplification (HDA), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470). For example, the modified detergents may be used in, for example, various ligation-mediated reactions, where for example ligation probes are employed as opposed to PCR primers. Additional exemplary methods include polymerase chain reaction (PCR; see, e.g., U.S. Pat. Nos. 4,683, 202; 4,683,195; 4,965,188; and/or 5,035,996), isothermal procedures (using one or more RNA polymerases (see, e.g., PCT Publication No. WO 2006/081222), strand displacement (see, e.g., U.S. Patent No. RE39007E), partial destruction of primer molecules (see, e.g., PCT Publication No. WO 2006/087574)), ligase chain reaction (LCR) (see, e.g., Wu, et al., *Genomics* 4: 560-569 (1990)), and/or Barany, et al. *Proc. Natl. Acad. Sci. USA* 88:189-193 (1991)), Qβ RNA replicase systems (see, e.g., PCT Publication No. WO 1994/016108), RNA transcription-based systems (e.g., TAS, 3SR), rolling circle amplification (RCA) (see, e.g., U.S. Pat. No. 5,854, 033; U.S. Patent Application Publication No. 2004/265897; Lizardi et al. *Nat. Genet.* 19: 225-232 (1998); and/or Banér et al. *Nucleic Acid Res.*, 26: 5073-5078 (1998)), and strand displacement amplification (SDA) (Little, et al. *Clin. Chem.* 45:777-784 (1999)), among others. These systems, along with the many other systems available to the skilled artisan, may be suitable for use in polymerizing and/or amplifying target nucleic acids for use as described herein.

"Amplification efficiency" may refer to any product that may be quantified to determine copy number (e.g., the term may refer to a PCR amplicon, an LCR ligation product, and/or similar product). The amplification and/or polymerization efficiency may be determined by various methods known in the art, including, but not limited to, determination of calibration dilution curves and slope calculation, determination using qBase software as described in Hellemans et al., *Genome Biology* 8:R19 (2007), determination using the delta delta Cq ($\Delta\Delta$Cq) calculation as described by Livak and Schmittgen, *Methods* 25:402 (2001), or by the method as described by Pfaffl, *Nucl. Acids Res.* 29:e45 (2001), all of which are herein incorporated by reference in their entirety.

In certain embodiments, amplification techniques comprise at least one cycle of amplification, for example, but not limited to, the steps of: denaturing a double-stranded nucleic acid to separate the component strands; hybridizing a primer to a target flanking sequence or a primer-binding site of an amplicon (or complements of either, as appropriate); and synthesizing a strand of nucleotides in a template-dependent manner using a DNA polymerase. The cycle may or may not be repeated. In certain embodiments, a cycle of amplification comprises a multiplicity of amplification cycles, for example, but not limited to 20 cycles, 25 cycles, 30 cycles, 35 cycles, 40 cycles, 45 cycles or more than 45 cycles of amplification.

In some embodiments, amplifying comprises thermocycling using an instrument, for example, but not limited to, a GeneAmp® PCR System 9700, 9600, 2700 or 2400 thermocycler, an Applied Biosystems® ViiA™ 7 Real-Time PCR System, an Applied Biosystems® 7500 Fast Real-Time PCR System, a 7900HT Fast Real-Time PCR System, and the like (all available from Life Technologies Corp., Carlsbad, Calif.). In certain embodiments, single-stranded amplicons are generated in an amplification reaction, for example, but not limited to asymmetric PCR or A-PCR.

In some embodiments, amplification comprises a two-step reaction including without limitation, a pre-amplification step wherein a limited number of cycles of amplification occur (for example, but not limited to, 2, 3, 4, or 5 cycles of amplification), then the resulting amplicon is generally diluted and portions of the diluted amplicon are subjected to additional cycles of amplification in a subsequent amplification step (see, e.g., U.S. Pat. No. 6,605,451 and U.S. Patent Application Publication No. 2004/0175733).

In certain embodiments, an amplification reaction comprises multiplex amplification, in which a multiplicity of different target nucleic acids and/or a multiplicity of different amplification product species are simultaneously amplified using a multiplicity of different primer sets. In certain embodiments, a multiplex amplification reaction and a single-plex amplification reaction, including a multiplicity of single-plex or lower-plexy reactions (for example, but not limited to a two-plex, a three-plex, a four-plex, a five-plex or a six-plex reaction) are performed in parallel.

Exemplary methods for polymerizing and/or amplifying nucleic acids include, for example, polymerase-mediated extension reactions. For instance, the polymerase-mediated extension reaction can be the polymerase chain reaction (PCR). In other embodiments, the nucleic acid amplification reaction is a multiplex reaction. For instance, exemplary methods for polymerizing and/or amplifying and detecting nucleic acids suitable for use as described herein are commercially available as TaqMan® (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety). TaqMan® assays are typically carried out by performing nucleic acid amplification on a target polynucleotide using a nucleic acid polymerase having 5'-to-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

As used herein, the term "detector probe" refers to a molecule used in an amplification reaction, typically for quantitative or real-time PCR analysis, as well as end-point analysis. Such detector probes can be used to monitor the amplification of the target polynucleotide. In some embodiments, detector probes present in an amplification reaction are suitable for monitoring the amount of amplicon(s) produced as a function of time. Such detector probes include, but are not limited to, the 5'-exonuclease assay (TaqMan® probes described herein (see also U.S. Pat. No. 5,538,848) various stem-loop molecular beacons (see e.g., U.S. Pat. Nos. 6,103,476 and 5,925,517 and Tyagi and Kramer, Nature Biotechnology 14:303-308 (1996)), stemless or linear beacons (see, e.g., PCT Publication No. WO 99/21881), PNA Molecular Beacons™ (see, e.g., U.S. Pat. Nos. 6,355,421 and 6,593,091), linear PNA beacons (see, e.g., Kubista et al., SPIE 4264:53-58 (2001)), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., Nucleic Acids Research 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., Methods 25:463-471 (2001); Whitcombe et al., Nature Biotechnology, 17:804-807 (1999); Isacsson et al., Molecular Cell Probes, 14:321-328 (2000); Svanvik et al., Anal Biochem. 281:26-35 (2000); Wolffs et al., Biotechniques 766: 769-771 (2001); Tsourkas et al., Nucleic Acids Research, 30:4208-4215 (2002); Riccelli et al., Nucleic Acids Research 30:4088-4093 (2002); Zhang et al., Shanghai. 34:329-332 (2002); Maxwell et al., J. Am. Chem. Soc. 124:9606-9612 (2002); Broude et al., Trends Biotechnol. 20:249-56 (2002); Huang et al., Chem Res. Toxicol. 15:118-126 (2002); and Yu et al., J. Am. Chem. Soc 14:11155-11161 (2001). Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescein dyes with $SO_3$ instead of the carboxylate group, phosphoramidite forms of fluorescein, phosphoramidite forms of Cy5 (commercially available for example from GE Healthcare). In some embodiments, interchelating labels are used such as ethidium bromide, SYBR® Green I (Life Technologies Corp., Carlsbad, Calif.), and PicoGreen® (Life Technologies Corp.), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69° C., though it will be appreciated that guided by the present teachings routine experimentation can result in detector probes with other Tms. In some embodiments, probes can further comprise various modifications such as a minor groove binder (see for example U.S. Pat. No. 6,486,308) to further provide desirable thermodynamic characteristics. In some embodiments, detector probes can correspond to identifying portions or identifying portion complements.

Another exemplary system suitable for use as described herein utilizes double-stranded probes in displacement hybridization methods (see, e.g., Morrison et al. *Anal. Biochem.*, 18:231-244 (1989); and/or Li, et al. *Nucleic Acids Res.*, 30(2,e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for polymerizing and/or amplifying and detecting target nucleic acids suitable for use as described herein involve "molecular beacons", which are single-stranded hairpin-shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher moiety that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA®), a single step isothermal process for polymerizing and/or amplifying RNA to double stranded DNA without temperature cycling. A NASBA reaction typically requires avian myeloblastosis virus (AMV), reverse transcriptase (RT), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpions™ system is another exemplary assay format that may be used in the methods described herein. Scorpions™ primers are bi-functional molecules in which a primer is covalently linked to the probe, along with a detectable label (e.g., a fluorophore) and a non-detectable quencher moiety that quenches the fluorescence of the detectable label. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., a hexaethylene glycol (HEG) monomer (Whitcombe, et al. *Nat. Biotech.* 17: 804-807 (1999)) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpions™ system may be used to examine and identify point mutations using multiple probes that may be differently tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for such labeled probes are known in the art and would be suitable for use in the methods described herein.

In some embodiments, the methods are performed before or in conjunction with a sequencing reaction. The term "sequencing" is used in a broad sense herein and refers to any technique known in the art that allows the order of at least some consecutive nucleotides in at least part of a polynucleotide, for example but not limited to a target nucleic acid or an amplicon, to be identified. Some non-limiting examples of sequencing techniques include Sanger's dideoxy terminator method and the chemical cleavage method of Maxam and Gilbert, including variations of those methods; sequencing by hybridization; sequencing by synthesis; and restriction mapping. Some sequencing methods comprise electrophoresis, including capillary electrophoresis and gel electrophoresis; sequencing by hybridization including microarray hybridization; mass spectrometry; single molecule detection; and ion/proton detection. In some embodiments, sequencing comprises direct sequencing, duplex sequencing, cycle sequencing, single base extension sequencing (SBE), solid-phase sequencing, or combinations thereof. In some embodiments, sequencing comprises detecting the sequencing product using an instrument, for example but not limited to an ABI Prism® 377 DNA Sequencer, an ABI Prism® 310, 3100, 3100-Avant, 3730 or 3730x1 Genetic Analyzer, an ABI Prism® 3700 DNA Analyzer, an Ion PGM™ sequencer, or an Ion Proton™ sequencer (all available from Life Technologies Corp., Carlsbad, Calif.), or a mass spectrometer. In some embodiments, sequencing comprises incorporating a dNTP, including a dATP, a dCTP, a dGTP, a dTTP, a dUTP, a dITP, or combinations thereof, and including dideoxyribonucleotide analogs of dNTPs, into an amplification product.

The term "DNA polymerase" is used herein in a broad sense and refers to any polypeptide that can catalyze the 5'-to-3' extension of a hybridized primer by the addition of deoxyribonucleotides and/or certain nucleotide analogs in a template-dependent manner. For example, but not limited to, the sequential addition of deoxyribonucleotides to the 3'-end of a primer that is annealed to a nucleic acid template during a primer extension reaction. Non-limiting examples of DNA polymerases include RNA-dependent DNA polymerases, including without limitation, reverse transcriptases, and DNA-dependent DNA polymerases. It is to be appreciated that certain DNA polymerases (for example, but not limited to certain eubacterial Type A DNA polymerases and Taq DNA polymerase) may further comprise a structure-specific nuclease activity and that when an amplification reaction comprises an invasive cleavage reaction.

The nucleic acid polymerases that may be employed in the disclosed nucleic acid amplification reactions may be any that function to carry out the desired reaction including, for example, a prokaryotic, fungal, viral, bacteriophage, plant, and/or eukaryotic nucleic acid polymerase. As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'-to-3' direction. Since DNA polymerase can only add a nucleotide onto a pre-existing 3'-OH group, to begin a DNA synthesis reaction, the DNA polymerase needs a primer to which it can add the first nucleotide. Suitable primers may comprise oligonucleotides of RNA or DNA, or chimeras thereof (e.g., RNA/DNA chimerical primers). The DNA polymerases may be a naturally occurring DNA polymerases or a variant of natural enzyme having the above-mentioned activity. For example, it may include a DNA polymerase having a strand displacement activity, a DNA polymerase lacking 5'-to-3' exonuclease activity, a DNA polymerase having a reverse transcriptase activity, or a DNA polymerase having an endonuclease activity.

Suitable nucleic acid polymerases may also comprise holoenzymes, functional portions of the holoenzymes, chimeric polymerase, or any modified polymerase that can effectuate the synthesis of a nucleic acid molecule. Within this disclosure, a DNA polymerase may also include a polymerase, terminal transferase, reverse transcriptase, telomerase, and/or polynucleotide phosphorylase. Non-limiting examples of polymerases may include, for example, T7 DNA polymerase, eukaryotic mitochondrial DNA Polymerase γ, prokaryotic DNA polymerase I, II, III, IV, and/or V; eukaryotic polymerase α, β, γ, δ, ε, η, ζ, ι, and/or κ; *E. coli* DNA polymerase I; *E. coli* DNA polymerase III alpha and/or epsilon subunits; *E. coli* polymerase IV, *E. coli* polymerase V; *T. aquaticus* DNA polymerase I; *B. stearothermophilus* DNA polymerase I; *Euryarchaeota* polymerases; terminal deoxynucleotidyl transferase (TdT); *S. cerevisiae* polymerase 4; translesion synthesis polymerases; reverse transcriptase; and/or telomerase. Non-limiting examples of suitable thermostable DNA polymerases that may be used include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the present teachings. Generally, any type I DNA polymerase may be used in accordance with the present teachings although other DNA polymerases may be used including, but not limited to, type III or family A, B, C etc. DNA polymerases. In addition, any genetically engineered DNA polymerases, any having reduced or insignificant 3'-to-5' exonuclease activity (e.g., SuperScript™ DNA polymerase), and/or genetically engineered DNA polymerases (e.g., those having the active site mutation F667Y or the equivalent of F667Y (e.g., in Tth), AmpliTaeFS, ThermoSequenase™), AmpliTaq® Gold, Platinum® Taq DNA Polymerase, Terminator I, Terminator II, Terminator III, Terminator Gamma (all available from New England Biolabs, Beverly, Mass.), and/or any derivatives and fragments thereof, may be used in accordance with the present teachings. Other nucleic acid polymerases may also be suitable as would be understood by one of skill in the art.

Polymerases used in accordance with the present teachings may be any enzyme that can synthesize a nucleic acid molecule from a nucleic acid template, typically in the 5' to 3' direction. The nucleic acid polymerases used in the methods disclosed herein may be mesophilic or thermophilic. Exemplary mesophilic DNA polymerases include T7 DNA polymerase, T5 DNA polymerase, Klenow fragment DNA polymerase, DNA polymerase III and the like. Exemplary thermostable DNA polymerases that may be used in the methods of the present teachings include Taq, Tne, Tma, Pfu, Tfl, Tth, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; PCT Publication Nos. WO 92/06188, WO 92/06200, and WO 96/10640; Barnes, *Gene* 112:29-35 (1992); Lawyer, et al., *PCR Meth. Appl.* 2:275-287 (1993); Flaman, et al., *Nucl. Acids Res.* 22(15): 3259-3260 (1994)). Examples of DNA polymerases substantially lacking in 3' exonuclease activity include, but are not limited to, Taq, Tne (exo-), Tma (exo-), Pfu (exo-), Pwo(exo-) and Tth DNA polymerases, and mutants, variants and derivatives thereof.

DNA polymerases for use in the methods disclosed herein may be obtained commercially, for example, from Life Technologies Corp. (Carlsbad, Calif.), Pharmacia (Piscataway, N.J.), Sigma (St. Louis, Mo.) and Boehringer Mannheim.

Enzymes for use in the compositions, methods, compositions and kits provided herein may also include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, et al., *Science* 239:487-491 (1988); U.S. Pat. Nos. 4,889,818 and 4,965,188), Tne DNA polymerase (PCT Publication No. WO 96/10640), Tma DNA polymerase (U.S. Pat. No. 5,374,553) and mutants, fragments, variants or derivatives thereof (see, e.g., commonly owned, co-pending U.S. patent application Ser. Nos. 08/706,702 and 08/706,706, both filed Sep. 9, 1996, which are incorporated by reference herein in their entireties). As will be understood by one of ordinary skill in the art, modified reverse transcriptases and DNA polymerase having reverse transcriptase activity may be obtained by recombinant or genetic engineering techniques that are well-known in the art. Mutant reverse transcriptases or polymerases may, for example, be obtained by mutating the gene or genes encoding the reverse transcriptase or polymerase of interest by site-directed or random mutagenesis. Such mutations may include point mutations, deletion mutations and insertional mutations. In some embodiments, one or more point mutations (e.g., substitution of one or more amino acids with one or more different amino acids) are used to construct mutant reverse transcriptases or polymerases for use in the invention. Fragments of reverse transcriptases or polymerases may also be obtained by deletion mutation by recombinant techniques that are well-known in the art, or by enzymatic digestion of the reverse transcriptase(s) or polymerase(s) of interest using any of a number of well-known proteolytic enzymes.

In some embodiments, enzymes for use in the methods provided herein include those that are reduced or substantially reduced in RNase H activity. Such enzymes that are reduced or substantially reduced in RNase H activity may be obtained by mutating the RNase H domain within the reverse transcriptase of interest, for example, by one or more point mutations, one or more deletion mutations, or one or more insertion mutations as described above. An enzyme "substantially reduced in RNase H activity" refers to an enzyme that has less than about 30%, less than about 25%, less than about 20%, less than about 15%, less than about 10%, less than about 7.5%, or less than about 5%, or less than about 5% or less than about 2%, of the RNase H activity of the corresponding wild type or RNase H+ enzyme such as wild type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, et al., *Nucl. Acids Res.* 16:265 (1988), in Gerard, et al., *FOCUS* 14(5):91 (1992), and in U.S. Pat. No. 5,668,005, the disclosures of all of which are fully incorporated herein by reference.

Polypeptides having reverse transcriptase activity for use in the methods provided herein may be obtained commercially, for example, from Life Technologies Corp. (Carlsbad, Calif.), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, et al., *J. Virol.* 29:517 (1979)). In addition, the polypeptides having reverse transcriptase activity may be prepared by recombinant DNA techniques that are familiar to one of ordinary skill in the art (see, e.g., Kotewicz, et al., *Nucl. Acids Res.* 16:265 (1988); Soltis and Skalka, *Proc. Natl. Acad. Sci. USA* 85:3372-3376 (1988)).

Exemplary polypeptides having reverse transcriptase activity for use in the methods provided herein include M-MLV reverse transcriptase, RSV reverse transcriptase, AMV reverse transcriptase, Rous Associated Virus (RAV) reverse transcriptase, Myeloblastosis Associated Virus (MAV) reverse transcriptase and Human Immunodeficiency Virus (HIV) reverse transcriptase, and others described in WO 98/47921 and derivatives, variants, fragments or mutants thereof, and combinations thereof. In a further embodiment, the reverse transcriptases are reduced or substantially reduced in RNase H activity, and may be selected from the group consisting of M-MLV H– reverse transcriptase, RSV H– reverse transcriptase, AMV H– reverse transcriptase, RAV H– reverse transcriptase, MAV H– reverse transcriptase and HIV H– reverse transcriptase, and derivatives, variants, fragments or mutants thereof, and combinations thereof. Reverse transcriptases of particular interest include AMV RT and M-MLV RT, and optionally AMV RT and M-MLV RT having reduced or substantially reduced RNase H activity (e.g., AMV RT alpha H–/BH+ and M-MLV RT H–). Reverse transcriptases for use in the invention include SuperScript™, SuperScript™II, ThermoScript™ and ThermoScript™ II available from Life Technologies Corp. See generally, PCT Publication No. WO 98/47921, U.S. Pat. Nos. 5,244,797 and 5,668,005, the entire contents of each of which are herein incorporated by reference.

In another aspect, the present disclosure provides reaction mixtures for polymerizing and/or amplifying a nucleic acid sequence of interest (e.g., a target sequence). In some embodiments, the reaction mixture may further comprise a detectable label. The methods may also include one or more steps for detecting the detectable label to quantitate the amplified nucleic acid. As used herein, the term "detectable label" refers to any of a variety of signaling molecules indicative of amplification. For example, SYBR® Green and other DNA-binding dyes are detectable labels. Such detectable labels may comprise or may be, for example, nucleic acid intercalating agents or non-intercalating agents. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent may produce a detectable signal directly or indirectly. The signal may be detectable directly using, for example, fluorescence and/or absorbance, or indirectly using, for example, any moiety or ligand that is detectably affected by proximity to double-stranded nucleic acid is suitable such as a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (see, e.g., U.S. Pat. Nos. 5,994,056; 6,171,785; and/or 6,814,934). Similarly, actinomycin D fluoresces in the red portion of the UV/VIS spectrum when bound to single-stranded nucleic acids, and fluoresces in the green portion of the UV/VIS spectrum when bound to double-stranded nucleic acids. And in another example, the photoreactive psoralen 4-aminomethyl-4-5',8-trimethylpsoralen (AMT) has been reported to exhibit decreased absorption at long wavelengths and fluorescence upon intercalation into double-stranded DNA (Johnson et al. *Photochem. & Photobiol.*, 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binders as described herein such as Hoechst 33258, distamycin, netropsin) may also be suitable for use. For example, Hoechst 33258 (Searle, et al. *Nucl. Acids Res.* 18(13):3753-3762 (1990)) exhibits altered fluorescence with an increasing amount of target. Minor groove binders are described in more detail elsewhere herein.

Other DNA binding dyes are available to one of skill in the art and may be used alone or in combination with other agents and/or components of an assay system. Exemplary DNA binding dyes may include, for example, acridines (e.g., acridine orange, acriflavine), actinomycin D (Jain, et al. *J. Mol. Biol.* 68:21 (1972)), anthramycin, BOBO™-1, BOBO™-3, BO-PRO™-1, cbromomycin, DAPI (Kapuseinski, et al. *Nucl. Acids Res.* 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Cambrex Bio Science Rockland Inc., Rockland, Me.), Hoechst 33258 (Searle and Embrey, *Nucl. Acids Res.* 18:3753-3762 (1990)), Hoechst 33342, homidium, JO-PRO™-1, LIZ dyes, LO-PRO™-1, mepacrine, mithramycin, NED dyes, netropsin, 4',6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX® blue, SYTOX® green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Aldrich Chemical Co., Milwaukee, Wis.), TOTO™-3, YO-PRO®-1, and YOYO®-3 (Life Technologies Corp., Carlsbad, Calif.), among others. SYBR® Green I (see, e.g., U.S. Pat. Nos. 5,436,134; 5,658,751; and/or 6,569,927), for example, has been used to monitor a PCR reactions. Other DNA binding dyes may also be suitable as would be understood by one of skill in the art.

For use as described herein, one or more detectable labels and/or quenching agents may be attached to one or more primers and/or probes (e.g., detectable label). The detectable label may emit a signal when free or when bound to one of the target nucleic acids. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorphore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluorosceins (e.g., 5-carboxy-2,7-dichlorofluorescein; 5-Carboxyfluorescein (5-FAM); 5-Hydroxy Tryptamine (5-HAT); 6-JOE; 6-carboxyfluorescein (6-FAM); FITC; 6-carboxy-1,4-dichloro-2',7'-dichlorofluorescein (TET); 6-carboxy-1,4-dichloro-2',4',5',7'-tetrachlorofluorescein (HEX); 6-carboxy-4',5'-dichloro-2',7'-dimethoxyfluorescein (JOE); Alexa Fluor® fluorophores (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP. EGFP), blue fluorescent protein (e.g., BFP, EBFP, EBFP2, Azurite, mKalama1), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker® and LysoSensor™ (e.g., LysoTracker® Blue DND-22, LysoTracker® Blue-White DPX, LysoTracker® Yellow HCK-123, LysoTracker® Green DND-26, LysoTracker® Red DND-99, LysoSensor™ Blue DND-167, LysoSensor™ Green DND-189, LysoSensor™ Green DND-153, LysoSensor™ Yellow/Blue DND-160, LysoSensor™ Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethylrhodamine), Tetramethylrhodamine (TRITC), WT), Texas Red, Texas Red-X, VIC and other labels described in, e.g., U.S. Patent Application Publication No. 2009/0197254 (incorporated herein by reference in its entirety), among others as would be known to those of skill in the art. Other detectable labels may also be used (see, e.g., U.S. Patent Application Publication No. 2009/0197254 (incorporated herein by reference in its entirety)), as would be known to those of skill in the art. Any of these systems and detectable labels, as well as many others, may be used to detect amplified target nucleic acids.

Some detectable labels may be sequence-based (also referred to herein as "locus-specific detectable label"), for example 5'-nuclease probes. Such probes may comprise one or more detectable labels. Various detectable labels are known in the art, for example (TaqMan® probes described herein (See also U.S. Pat. No. 5,538,848 (incorporated herein by reference in its entirety)) various stem-loop molecular beacons (See, e.g., U.S. Pat. Nos. 6,103,476 and 5,925,517 and Tyagi and Kramer, *Nature Biotechnology* 14:303-308 (1996)), stemless or linear beacons (See, e.g., PCT Publication No. WO 99/21881; U.S. Pat. No. 6,485,901), PNA Molecular Beacons™ (See, e.g., U.S. Pat. Nos. 6,355,421 and 6,593,091), linear PNA beacons (See, e.g., Kubista et al., *SPIE* 4264:53-58 (2001)), non-FRET probes (See, e.g., U.S. Pat. No. 6,150,097), Sunrise®/Amplifluor® probes (U.S. Pat. No. 6,548,250), stem-loop and duplex Scorpions™ probes (Solinas et al., *Nucleic Acids Research* 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596, 490), peptide nucleic acid (PNA) light-up probes (Svanvik, et al. *Anal Biochem* 281:26-35 (2001)), self-assembled nanoparticle probes, ferrocene-modified probes described, for example, in U.S. Pat. No. 6,485,901; Mhlanga et al., *Methods* 25:463-471 (2001); Whitcombe et al., *Nature Biotechnology.* 17:804-807 (1999); Isacsson et al., *Molecular Cell Probes.* 14:321-328 (2000); Svanvik et al., *Anal Biochem.* 281:26-35 (2000); Wolffs et al., *Biotechniques* 766:769-771 (2001); Tsourkas et al., *Nucleic Acids Research.* 30:4208-4215 (2002); Riccelli et al., *Nucleic Acids Research* 30:4088-4093 (2002); Zhang et al., *Acta Biochimica et Biophysica Sinica (Shanghai).* 34:329-332 (2002); Maxwell et al., *J. Am. Chem. Soc.* 124:9606-9612 (2002); Broude et al., *Trends Biotechnol.* 20:249-56 (2002); Huang et al., *Chem Res. Toxicol.* 15:118-126 (2002); and Yu et al., *J. Am. Chem. Soc.* 14:11155-11161 (2001); QuantiProbes® (www.qiagen.com), HyBeacons® (French, et al. *Mol. Cell. Probes* 15:363-374 (2001)), displacement probes (Li, et al. *Nucl. Acids Res.* 30:e5 (2002)), HybProbes (Cardullo, et al. *Proc. Natl. Acad. Sci. USA* 85:8790-8794 (1988)), MGB Alert (www.nanogen.com), Q-PNA (Fiandaca, et al. *Genome Res.* 11:609-611 (2001)), Plexor® (www.Promega.com), LUX™ primers (Nazarenko, et al. *Nucleic Acids Res.* 30:e37 (2002)), DzyNA primers (Todd, et al. *Clin. Chem.* 46:625-630 (2000)). Detectable labels may also comprise non-detectable quencher moieties that quench the fluorescence of the detectable label, including, for example, black hole quenchers (Biosearch), Iowa Black® quenchers (IDT), QSY quencher (Molecular Probes), and Dabsyl and Dabcyl sulfonate/carboxylate Quenchers (Epoch). Detectable labels may also comprise two probes, wherein for example a fluorophore is on one probe, and a quencher is on the other, wherein hybridization of the two probes together on a target quenches the signal, or wherein hybridization on a target alters the signal signature via a change in fluorescence. Exemplary systems may also include FRET, salicylate/DTPA ligand systems (see, e.g., Oser et al. *Angew. Chem. Int. Engl.* 29(10):1167 (1990)), displacement hybridization, homologous probes, and/or assays described in European Patent No. EP 070685 and/or U.S. Pat. No. 6,238,927. Detectable labels can also comprise sulfonate derivatives of fluorescein dyes with $SO_3$ instead of the carboxylate group, phosphoramidite forms of fluorescein, phosphoramidite forms of Cy5 (available for example from GE Healthcare). All references cited above are hereby incorporated herein by reference in their entirety.

The compositions and methods described herein may be useful for detecting and/or quantifying a variety of target nucleic acids from a test sample. A target nucleic acid is any nucleic acid for which an assay system is designed to identify or detect as present (or not), and/or quantify in a test sample. Such nucleic acids may include, for example, those of infectious agents (e.g., virus, bacteria, parasite, and the like), a disease process such as cancer, diabetes, or the like, or to measure an immune response. Exemplary "test samples" include various types of samples, such as biological samples. Exemplary biological samples include, for instance, a bodily fluid (e.g., blood, saliva, spinal fluid), a tissue sample, a food (e.g., meat) or beverage (e.g., milk) product, or the like. Expressed nucleic acids may include, for example, genes for which expression (or lack thereof) is associated with medical conditions such as infectious disease (e.g., bacterial, viral, fungal, protozoal infections) or cancer. The methods described herein may also be used to detect contaminants (e.g., bacteria, virus, fungus, and/or protozoan) in pharmaceutical, food, or beverage products. The methods described herein may be also be used to detect rare alleles in the presence of wild type alleles (e.g., one mutant allele in the presence of $10^6$-$10^9$ wild type alleles). The methods are useful to, for example, detect minimal residual disease (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine).

The detection of the signal may be using any reagents or instruments that detect a change in fluorescence from a fluorophore. For example, detection may be performed using any spectrophotometric thermal cycler. Examples of spectrophotometric thermal cyclers include, but are not limited to, Applied Biosystems (AB) PRISM® 7000, AB 7300 real-time PCR system, AB 7500 real-time PCR system, AB PRISM® 7900HT, Bio-Rad ICycler IQ™, Cepheid SmartCycler® II, Corbett Research Rotor-Gene 3000, Idaho Technologies R.A.P.I.D.™, MJ Research Chromo 4™, Roche Applied Science LightCycler®, Roche Applied Science LightCycler®2.0, Stratagene Mx3000P™, and Stratagene Mx4000™. It should be noted that new instruments are being developed at a rapid rate and any like instruments may be used for the methods.

Kits for performing the methods described herein are also provided. As used herein, the term "kit" refers to a packaged set of related components, typically one or more compounds or compositions. The kit may comprise a pair of oligonucleotides for polymerizing and/or amplifying at least one target nucleic acid from a sample, one or more detergents, a nucleic acid polymerase, and/or corresponding one or more probes labeled with a detectable label. The kit may also include samples containing pre-defined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. In one embodiment, the kit may include one or more of, for example, a buffer (e.g., Tris), one or more salts (e.g., KCl), glycerol, dNTPs (dA, dT, dG, dC, dU), recombinant BSA (bovine serum albumin), a dye (e.g., ROX passive reference dye), one or more detergents, polyethylene glycol (PEG), polyvinyl pyrrolidone (PVP), and/or gelatin (e.g., fish or bovine source). Other embodiments of particular systems and kits are also contemplated which would be understood by one of skill in the art.

The methods and compositions may be used for detection and quantification of nucleic acids in a sample. The sample may include one or more templates and/or one or more target nucleic acids. The sample may be purified or unpurified. The sample may be a biological sample, such as blood, saliva, tears, tissue, urine, stool, etc., that has been treated to use in the methods provided herein. Alternatively, if the biological sample does not interfere with the methods provided herein, it may be used untreated (or unpurified).

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLES

Example 1

Amplification Restriction by STAR Primers with Various Lengths of Overlap

Figure 3:
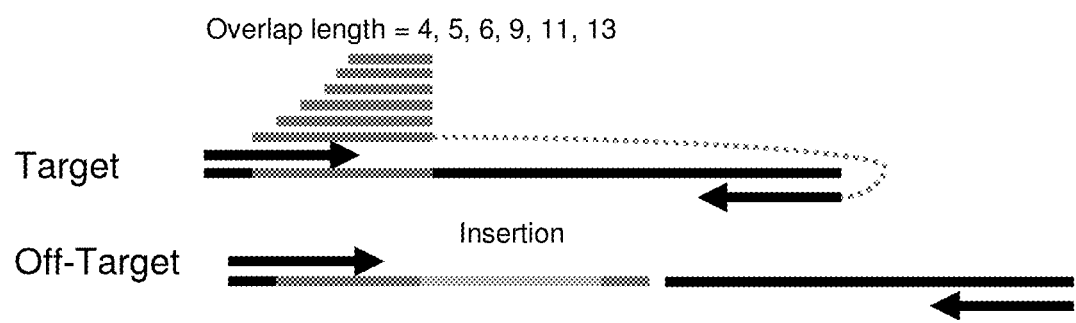
FIG. 3 schematically depicts STAR primers with various lengths of overlap with a primer binding site on target sequences.

STAR reverse primers were designed with different lengths of overlap (0, 4, 5, 6, 9, 11 and 13 nucleotides) with the forward primer binding site on the target sequence and used to evaluate their efficiency in suppressing target amplification. See, FIG. 3. Two target polynucleotides were used in the amplification reactions: a target sequence in which STAR region was intact and perfectly matched (PM) with the STAR tag sequence and an off-target sequence with an insertion (lin-4) between the $6^{th}$ and $7^{th}$ base from the 3' end of the STAR tag target region. In addition to a set of STAR primers with a perfectly matched (PM) STAR tag, a set of STAR primers with a single base C to A mismatch (MM) introduced at the STAR region was used. Real-time PCR was run with Power SYBR® Master Mix with 150 nM of each forward and reverse primers on Step-One Plus real-time PCR instrument (thermal cycling conditions: 95° C./10 min, 40 cycles of 95° C./15 sec and 60° C./1 min).

Figure 4:
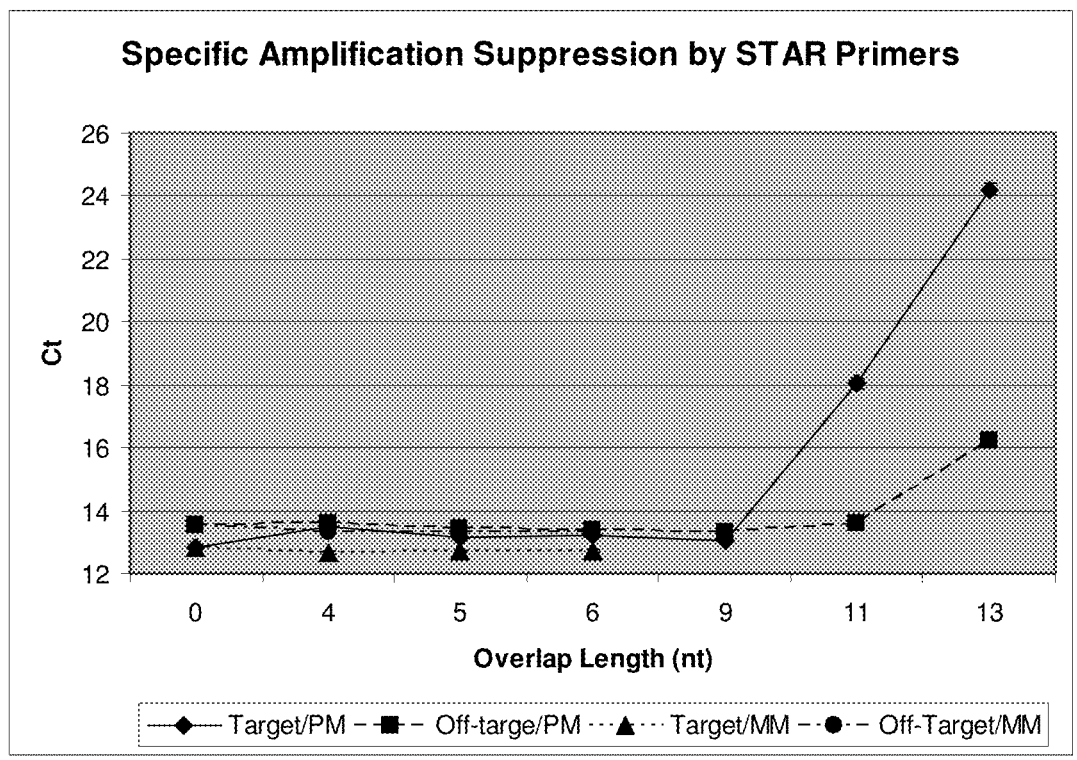
FIG. 4 graphically represents amplification suppression of target and off-target sequences by STAR primers with various overlap lengths: target sequence with perfectly matched (PM) STAR tag (diamond line), off-target sequence with PM STAR tag (square line), target sequence with mismatch (MM) STAR tag (triangle line), and off-target sequence with MM STAR tag (circle line).

Exemplary results are shown in FIG. 4. A $C_t$ shift was observed for the target starting with a 4 nucleotide overlap, while the MM STAR primer had no effect. Amplification of the target was drastically suppressed when the overlap reached 11 nucleotides, while the off-target amplification was not impacted. Increasing the overlap to 13 nucleotides increased the target $C_t$ by 13.4 and increased the off-target $C_t$ by 2.7.

Example 2

Suppression of Ligation Background and Improvement of miRNA Detection by STAR Primers The workflow shown in FIG. 4 is an example of a next generation TaqMan® miRNA assay as described in co-owned, co-pending U.S. Provisional Patent Application No. 61/721,968, filed Nov. 2, 2012, and PCT Application No. PCT/US2013/068350, entitled "Small RNA Capture, Detection and Quantification," filed concurrently herewith, each of which are herein incorporated by reference in its entirety. In this assay, ligation adaptors are ligated to the 5' and 3' ends of miRNA. In this ligation step however, adaptor-adaptor ligation byproducts can form and be subsequently amplified to create unwanted background in the assay.

Figure 5:
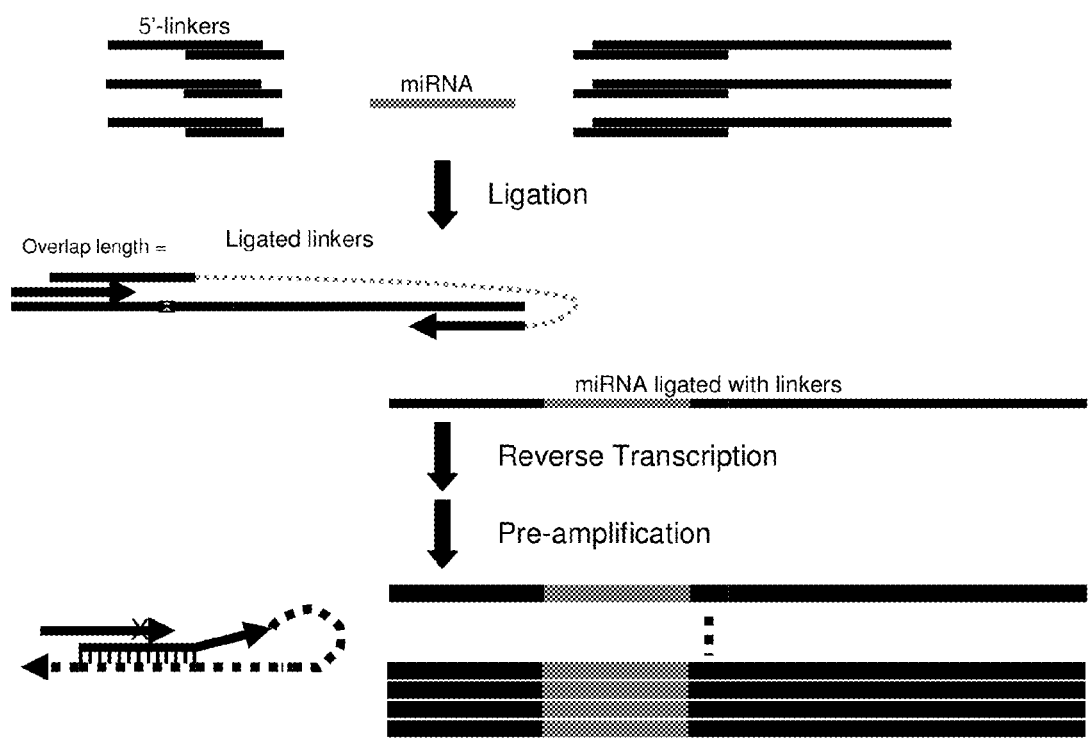
FIG. 5 schematically depicts an embodiment of a next generation TaqMan® miRNA assay workflow using 5' and 3' ligation adaptors (or linkers), 5' and 3' ligation splints, and a STAR primer.
Figure 6:
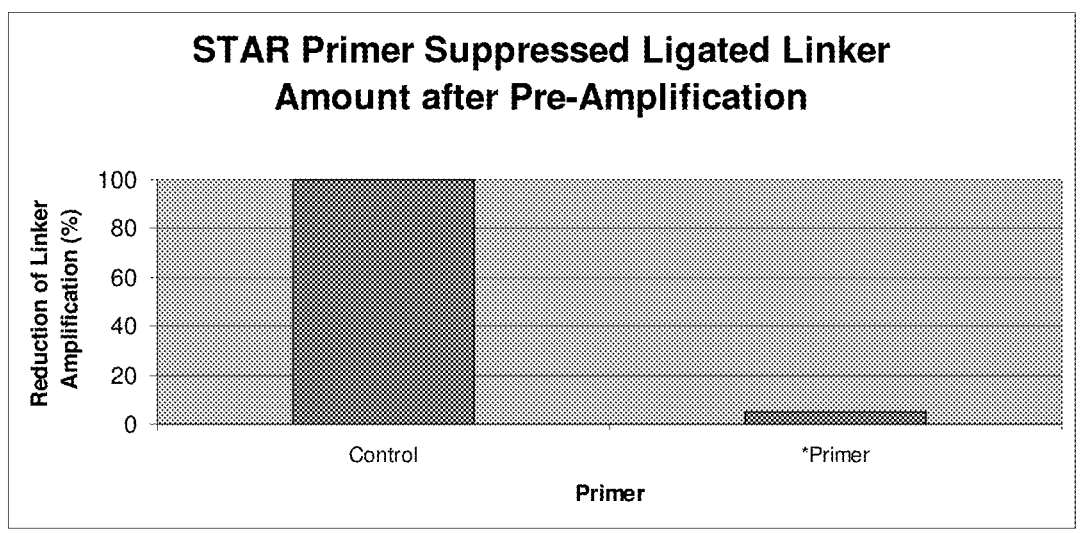
FIG. 6 graphically represents the reduction of adaptor (linker) amplification with use of the STAR primer compared to a control primer.
Figure 7:
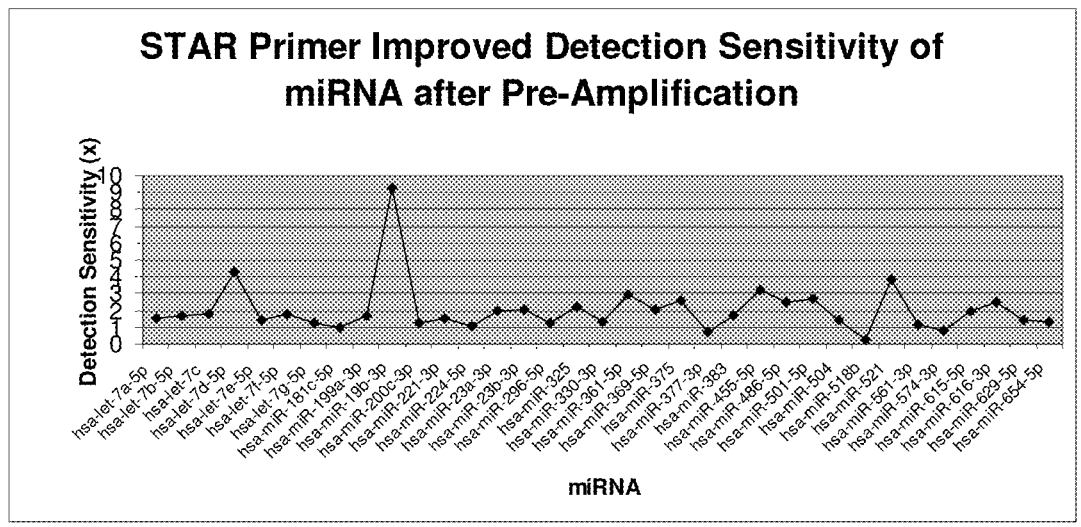
FIG. 7 graphically represents the increase in sensitivity of qPCR detection of target miRNA using a STAR primer compared to a control primer.

A STAR primer with a 12 nucleotide overlap with the forward primer was designed and tested in the dual-ended ligation miRNA assay. Total RNA plus 45 synthetic miRNA was first ligated to 5' and 3' ligation adaptors (referred to as "linkers" in FIG. 5), then reverse transcribed by SuperScript® III in RT buffer. One-tenth of the reverse transcribed material was amplified in a pre-amplification step by 12 cycles in a 1× pre-amplification master mix with 250 nM of each of the forward and reverse primers. A standard reverse primer was used as a control. Each miRNA target was amplified and detected on Vii7A real-time PCR instrument with its specific TaqMan® assay. For the detection assay, 900 nM each of forward and reverse primer and 250 nM TaqMan® probe were used in 1× Gene Expression Master Mix at standard thermal cycling conditions (95° C./10 min, 40 cycles of 95° C./15 sec and 60° C./1 min). Ct values were calculated with auto baseline and ΔRn threshold of 0.2. As shown in FIG. 6, the STAR primer significantly reduced the amount of ligated ligation adaptor amplification background. FIG. 7 shows the fold increase in detection sensitivity of each miRNA with the use of the STAR primer as compared to the use of the control standard reverse primer.

Example 3

Differentiation of Homologous miRNA by STAR Primers

Figure 8:
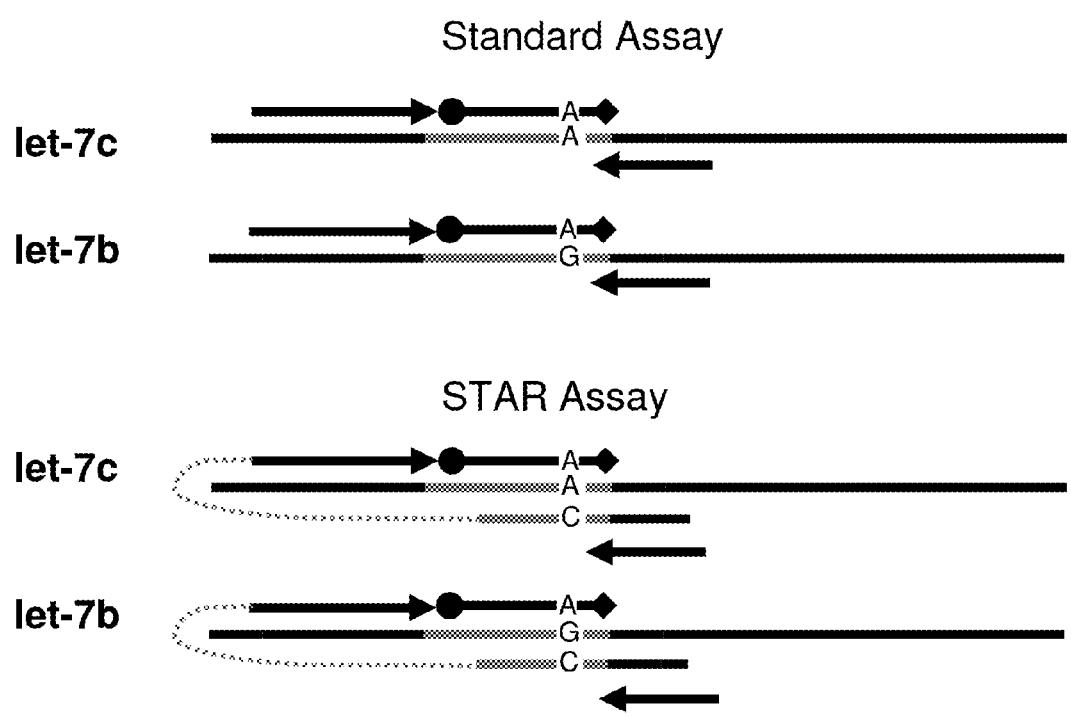
FIG. 8 schematically depicts assays for differentiation of human let-7c and let-7b miRNAs using a standard forward primer and using a STAR forward primer.

Human let-7 miRNAs are highly homologous, with a single base difference between let-7b and let-7c. A pair of standard primers that differentiated let-7b and let-7c from the rest of the family, but amplified both let-7b and let-7c were used. miRNA templates were generated as in Example 2 and PCR conditions were the similar as in Example 2 except 7900 HTS real-time PCR instrument was used. Even with a mismatched probe to let-7b, the standard assay detected both let-7b and let-7c equally (Table 1). The use of a STAR primer designed with a STAR tag sequence against let-7b (FIG. 8) for the amplification reaction suppressed the let-7b and let-7c cross-reactivity (calculated as $2^{\Delta Ct(c-b)}$) from 109% to 2% (see Table 1). Cross reactivity was calculated as $100/2^{\Delta Ct}$ (let-7c–let-7b).

TABLE 1

| Template | let-7b | let-7c |
|---|---|---|
| Std let-7c assay | 109% | 100% |
| STAR let-7c assay | 2% | 100% |

What is claimed is:

1. A composition comprising
   a first oligonucleotide primer comprising a 5' Sequence-Targeted Amplification Restrictive (STAR) tag sequence portion and a target nucleic acid hybridization sequence portion; and
   a second oligonucleotide primer comprising a target nucleic acid hybridization sequence portion, wherein the STAR tag sequence is the same as all or a portion of the target nucleic acid hybridization sequence of the second oligonucleotide primer and the STAR tag sequence is the same as a sequence in the target nucleic acid 5' of the first oligonucleotide target nucleic acid hybridization sequence hybridization site.

2. The composition of claim 1, wherein the sequence shared between the first and the second primers is between about 3 and about 15 nucleotides in length.

3. The composition of claim 1, wherein the first oligonucleotide primer and the second oligonucleotide primer are a pair of forward and reverse amplification primers.

4. The composition of claim 1 further comprising a polynucleotide extension product comprising the STAR tag sequence at the 5' end and a sequence complementary to the STAR tag sequence to the 3' side of the STAR tag sequence, wherein the STAR tag sequence and the complementary sequence render the extension product capable of forming a stem-loop structure.

5. A method of detecting a nucleic acid comprising:
   contacting the target nucleic acid with a composition of claim 1;
   hybridizing the target nucleic acid with the first oligonucleotide primer;
   extending the oligonucleotide to form an extension product;
   amplifying the extension product to form an amplification product; and
   detecting the presence or absence of the amplification product, thereby detecting the target nucleic acid.

6. A method of inhibiting or substantially blocking undesired amplification of a target nucleic acid comprising:
   contacting the target nucleic acid with a composition of claim 1;
   hybridizing the target nucleic acid with the first oligonucleotide primer;
   extending the oligonucleotide to form an extension product;
   incubating the extension product with an amplification reaction mixture; and
   detecting the presence or absence of the extension product.

7. A method of inhibiting or substantially blocking undesired amplification of a target nucleic acid comprising:
   contacting the target nucleic acid with a composition of claim 1;
   hybridizing the target nucleic acid with the first oligonucleotide primer; and
   extending the oligonucleotide to form an extension product, wherein the extension product inhibits or substantially reduces undesired amplification of the target nucleic acid.

8. The composition of claim 1, wherein the STAR tag sequence further comprises a sequence the same as a portion of an internal amplicon sequence of the target nucleic acid.

9. The composition of claim 1, wherein the STAR tag sequence is about 10 to about 40 nucleotides in length.

10. The composition of claim 2, wherein the sequence shared between the first and the second primers is 11, 12, or 13 nucleotides in length.

11. A composition comprising
   a first oligonucleotide primer comprising a 5' Sequence-Targeted Amplification Restrictive (STAR) tag sequence portion and a target nucleic acid hybridization sequence portion; and
   a second oligonucleotide primer comprising a target nucleic acid hybridization sequence portion, wherein the STAR tag sequence is complementary to all or a portion of the target nucleic acid hybridization sequence of the second oligonucleotide primer and the STAR tag sequence is the same as a sequence in the target nucleic acid 5' of the first oligonucleotide target nucleic acid hybridization sequence hybridization site.

12. The composition of claim 11, wherein the STAR tag sequence further comprises a sequence the same as an internal amplicon sequence of the target nucleic acid.

13. The composition of claim 11, wherein the STAR tag sequence is about 10 to about 40 nucleotides in length.

14. The composition of claim 11, wherein the complementary sequence between the first and the second primers is between about 3 and about 15 nucleotides in length.

15. The composition of claim 11 further comprising a polynucleotide extension product comprising the STAR tag sequence at the 5' end and a sequence complementary to the STAR tag sequence to the 3' side of the STAR tag sequence, wherein the STAR tag sequence and the complementary sequence render the extension product capable of forming a stem-loop structure.

* * * * *